United States Patent [19]

Krüger et al.

[11] Patent Number: 5,750,848
[45] Date of Patent: May 12, 1998

[54] DNA SEQUENCE USEFUL FOR THE PRODUCTION OF POLYHYDROXYALKANOATES

[75] Inventors: Niels Krüger, Billerbeck; Alexander Steinbüchel, Münster, both of Germany

[73] Assignee: Monsanto Company, St. Louis, Mo.

[21] Appl. No.: 700,576

[22] Filed: Aug. 13, 1996

[51] Int. Cl.$^6$ .................... A01H 5/00; C12N 1/20; C12N 1/21; C12N 5/14

[52] U.S. Cl. .................. 800/205; 435/172.3; 435/183; 435/252.3; 435/253.3; 435/320.1; 435/419; 435/252.34; 536/23.2; 536/23.7; 800/250; 800/DIG. 9; 800/DIG. 14; 800/DIG. 15; 800/DIG. 23; 800/DIG. 26; 800/DIG. 42; 800/DIG. 43; 800/DIG. 56; 800/DIG. 58; 530/350

[58] Field of Search ................ 530/350; 536/23.2, 536/23.7; 435/320.1, 410, 419, 243, 172.3, 183, 193, 252.3, 253.3, 252.34; 800/205, 250, DIG. 1, DIG. 14, DIG. 15, DIG. 23, DIG. 26, DIG. 42, DIG. 43, DIG. 56, DIG. 58

[56] References Cited

U.S. PATENT DOCUMENTS

| | | | |
|---|---|---|---|
| 5,135,859 | 8/1992 | Witholt et al. | 435/135 |
| 5,245,023 | 9/1993 | Peoples et al. | 536/27 |
| 5,344,769 | 9/1994 | Witholt et al. | 435/135 |
| 5,395,919 | 3/1995 | Lee et al. | 528/361 |
| 5,480,794 | 1/1996 | Peoples et al. | 435/232 |

FOREIGN PATENT DOCUMENTS

| | | |
|---|---|---|
| WO 93/02194 | 2/1993 | WIPO . |
| WO 94/11519 | 5/1993 | WIPO . |

OTHER PUBLICATIONS

Ochsner et al., "Production of Rhamnolipid Biosurfactants," *Advances in Biochemical Engineering/Biotechnology* 53:89–118 (1996).

van der Leij et al., "Strategies for th Sustainable Production of New Biodegradable Polyesters in Plants: A Review," *Can. J. Microbiol.* 41:222–238 (1995).

Ochsner et al., "Isolation and Characterization of a Regulatory Gene Affecting Rhamnolipid Biosurfactant Synthesis in *Pseudomonas aeruginosa*," *Journal of Bacteriology* 176:2044–2054 (1994).

Ochsner et al., "Autoinducer–Mediated Regulation of Rhamnolipid Biosurfactant Synthesis in *Pseudomonas aeruginosa*," *Proc. Natl. Acad. Sci. USA* 92:6424–6428 (1995).

Ochsner et al., "Isolation, Characterization, and Expression in *Escherichia coli* of the *Pseudomonas aeruginosa rhlAB* Genes Encoding a Rhamnosyltransferase Involved in Rhamnolipid Biosurfactant Synthesis", *Journal of Biological Chemistry* 269:19787–19795 (1994).

Koch et al., "Hydrocarbon Assimilation and Biosurfactant Production in *Pseudomonas aeruginosa* Mutants," *Journal of Bacteriology* 173:4212–4219 (1991).

GenBank accession L012105: Quinolone sensitivity protein from *P. aeruginosa* (1992).

*Primary Examiner*—David T. Fox
*Assistant Examiner*—Amy J. Nelson
*Attorney, Agent, or Firm*—Gary M. Bond; Arnold, White & Durkee

[57] ABSTRACT

A genomic fragment harboring the gene phaG was cloned by phenotypic complementation of *Pseudomonas putida* KT2440 mutants, defective in the polyhydroxyalkanoic acid (PHA) synthesis via de novo fatty acid biosynthesis but not affected in PHA biosynthesis via fatty acid β-oxidation. The 885-bp phaG gene encodes a protein of 295 amino acids with a molecular weight of 33,876 Da. The transcriptional induction of phaG could be observed under conditions of PHA synthesis via de novo fatty acid biosynthesis whereas no induction was detected under conditions which favor PHA synthesis via fatty acid degradation by β-oxidation. The phaG gene is useful for the production of PHAs in bacteria and plants.

26 Claims, 2 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
    ( A ) LENGTH: 3061 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1:

| | | | | | | |
|---|---|---|---|---|---|---|
| GAATTCAGCC | GCGTAGAGCT | GGACGAGCAA | CTGCTGCAGG | CCGGCCGCCC | GGCCCGCTAC | 60 |
| CTGATGCTGT | ACAAGCCCAC | TGGCTGCGTA | ACGGCCACCC | ACGATCCGCA | ACACCGTACC | 120 |
| GTTCTCGACC | TGCTGCCAGC | GGCGTTGCGA | GATGACCTGC | ACATAGCCGG | CGCCTGGAC | 180 |
| TTCAACACCA | CCGGCCTGAT | GATCCTGACC | AACGATGGCC | AATGGTCACG | GCGGCCTGAC | 240 |
| CAGCCTGCCA | CCAAGCTGCC | CAAGCATTAT | CTGGTGGACA | CCGAGGACGA | GATTGGCGAG | 300 |
| CACTATGTGG | CCAAGTTTCG | CGAGGGTTTC | TATTTTGCCT | TCGAAGACCT | CACCACCCAA | 360 |
| CCTGCCCAGC | TGGACATCCT | CGGCCCCCAC | CGAGCCCGGC | TGGCGATCGT | CGAGGGGCGT | 420 |
| TACCACCAGG | TCAAGCGCAT | GTTCGGGCAT | TTCAACAACA | AGGTGATCGG | GCTGCATCGG | 480 |
| GAGAGCATGG | GGGCGATCCG | GCTGGATCCG | GGGTTGGCGC | CGGGGGAGTA | TCGTGAACTG | 540 |
| ACGGCCAATG | AGATAGCCAC | TGTCTAGGCC | GTGACAGACA | GCCCGTGTCG | TCATACGACC | 600 |
| GCTCAGCGAC | AAAAGTCACA | TTACTTACCG | AACGGCACTT | GCGCGATCCC | CAACCCACTG | 660 |
| CTTGAATCCA | AATCGTCAGT | CTGCATGTGA | CTACCAAGTC | ACACCTGCAG | CCGATGACAC | 720 |
| TTTTTGCCGG | CCACCCAAAG | CCTAGATGCC | TTGGGGCACG | GCAAATTGCC | CGCCAAAAAC | 780 |
| AATACCGTCG | ACGCAAGTGC | CAAGGATCGA | CACAGGGCCC | CCGGATTATC | TTCAGGCAAA | 840 |
| TGCCTACCTG | TCATAAAGAA | CGTGCACCCT | AGGTGACGCG | AATACCCTTT | TTGCGCCAGG | 900 |
| AGTCGATGAC | ATGAGGCCAG | AAATCGCTGT | ACTTGATATC | CAAGGTCAGT | ATCGGGTTTA | 960 |
| CACGGAGTTC | TATCGCGCGG | ATGCGGCCGA | AAACACGATC | ATCCTGATCA | ACGGCTCGCT | 1020 |
| GGCCACCACG | GCCTCGTTCG | CCCAGACGGT | ACGTAACCTG | CACCCACAGT | TCAACGTGGT | 1080 |
| TCTGTTCGAC | CAGCCGTATT | CAGGCAAGTC | CAAGCCGCAC | AACCGTCAGG | AACGGCTGAT | 1140 |
| CAGCAAGGAG | ACCGAGGCGC | ATATCCTCCT | TGAGCTGATC | GAGCACTTCC | AGGCAGACCA | 1200 |
| CGTGATGTCT | TTTTCGTGGG | GTGGCGCAAG | CACGCTGCTG | GCGCTGGCGC | ACCAGCCGCG | 1260 |
| GTACGTGAAG | AAGGCAGTGG | TGAGTTCGTT | CTCGCCAGTG | ATCAACGAGC | CGATGCGCGA | 1320 |
| CTATCTGGAC | CGTGGCTGCC | AGTACCTGGC | CGCCTGCGAC | CGTTATCAGG | TCGGCAACCT | 1380 |
| GGTCAATGAC | ACCATCGGCA | AGCACTTGCC | GTCGCTGTTC | AAACGCTTCA | ACTACCGCCA | 1440 |
| TGTGAGCAGC | CTGGACAGCC | ACGAGTACGC | ACAGATGCAC | TTCCACATCA | ACCAGGTGCT | 1500 |
| GGAGCACGAC | CTGGAACGTG | CGCTGCAAGG | CGCGCGCAAT | ATCAACATCC | CGGTGCTGTT | 1560 |
| CATCAACGGC | GAGCGCGACG | AGTACACCAC | AGTCGAGGAT | GCGCGGCAGT | TCAGCAAGCA | 1620 |
| TGTGGGCAGA | AGCCAGTTCA | GCGTGATCCG | CGATGCGGGC | CACTTCCTGG | ACATGGAGAA | 1680 |
| CAAGACCGCC | TGCGAGAACA | CCCGCAATGT | CATGCTGGGC | TTCCTCAAGC | CAACCGTGCG | 1740 |
| TGAACCCCGC | CAACGTTACC | AACCCGTGCA | GCAGGGGCAG | CATGCATTTG | CCATCTGAGC | 1800 |
| GGCTCGGCGC | CTTGTAGCCA | ATACCCGCAG | GCCACGGGGC | GCCGACAAGC | TTTTTTATAA | 1860 |

-continued

```
CTTGGGCTTC TAATTCGCTG AAGGTTCTGG TAAAAAGTCG AGCTCAGATG CGGGTATAGT     1920
TTAGTGGCAA AACGAAAGCT TCCCAAGCTT TAGTTGAGGG TTCGATTCCC TCTACCCGCT     1980
CCACATCGCA GTCCCGCATG GCGTTCCAGC AACGTCATCG CAGTCAAAAG GAGCCTTGGC     2040
TCCTTTTTTC GTTTTCATC CTGCCTTGAC CTGGCCCATG GCCAATTACC CACCGATCCG      2100
CTTCAATGCG CATCGGGCCT TTGCGTGCGC AAGCGAAACG GCTTGTGGCG ATATGCTCA      2160
CTGGATTCGT GAAACTATTC GAAAGGACAA CGCATGTTTC TCTCCGCTG GCTACCGGGC      2220
CTTGCCAACC TGCTGCACTA CCGCCGTGAA TGGTTCCACG CCGATCTGCA AGCGGGCCTG     2280
TCGGTAGCCG CGATCCAGAT TCCCATTGCC ATTGCCTATG CGCAGATCGT CGGGCTGCCG     2340
CCGCAATATG GCCTGTACGC CTGTGTGCTA CCGATGATGG TCTACGCGCT GATCGGTAGC     2400
TCGCGCCAGC TGATGGTCGG CCCCGACGCC GCCACCTGCG CGATGATCGC CGGTGCCGTG     2460
GCACCGCTGG CCATGGGTGA CCCGCAGCGC ATCGTCGAAC TGTCGGTGAT CGTCACCGTG     2520
CTGGTCGGCG TGATGCTGAT TGCCGCGGGC CTGGCGCGGG CCGGGTTCAT CGCCAGCTTC     2580
TTCTCGCGGC CGATCCTGAT CGGCTACCTC AACGGTATCG GCCTGAGCCT GATCGCCGGG     2640
CAGCTGTCCA AGGTGGTGGG CTTCAAGATC GAGGGCGACG GTTTCATCCT CAGCCTGATC     2700
AACTTCTTCC AGCGCCTGGG GGAAATTCAC TGGGTCACAT TGATCATCGG CCTGGCCGCC     2760
CTGGGCCTGC TCATCTGGCT GCCACGGCGC TACCCGCGCC TGCCCGCAGC CCTCACGGTA     2820
GTGGCGCTGT TCATGCTGCT GGTTGGCCTG TTCGGCCTCG ACCGCTTCGG CGTTGCCGTC     2880
CTTGGGCCGG TACCTGCAGG CATCCCGCAA CTGGCCTGGC CACACAGCAA CCTGGCGGAA     2940
ATGAAGAGCC TGCTGCGGCG ACGCCCTGGG TATCGCCACC GTCAGCTTCT GCAGCGCCAT     3000
GCTTACCGCA CGCAGCTTTG CCGCCCGGCA TGGCTATGCG ATCAACGCCA ACCACGAATT     3060
C                                                                    3061
```

( 2 ) INFORMATION FOR SEQ ID NO:2:

( i ) SEQUENCE CHARACTERISTICS:
        ( A ) LENGTH: 295 amino acids
        ( B ) TYPE: amino acid
        ( C ) STRANDEDNESS:
        ( D ) TOPOLOGY: linear ( x i ) SEQUENCE DESCRIPTION: SEQ ID NO:2:

```
Met Arg Pro Glu Ile Ala Val Leu Asp Ile Gln Gly Gln Tyr Arg Val
 1               5                  10                  15
Tyr Thr Glu Phe Tyr Arg Ala Asp Ala Ala Glu Asn Thr Ile Ile Leu
            20                  25                  30
Ile Asn Gly Ser Leu Ala Thr Thr Ala Ser Phe Ala Gln Thr Val Arg
        35                  40                  45
Asn Leu His Pro Gln Phe Asn Val Val Leu Phe Asp Gln Pro Tyr Ser
    50                  55                  60
Gly Lys Ser Lys Pro His Asn Arg Gln Glu Arg Leu Ile Ser Lys Glu
65                  70                  75                  80
Thr Glu Ala His Ile Leu Leu Glu Leu Ile Glu His Phe Gln Ala Asp
                85                  90                  95
His Val Met Ser Phe Ser Trp Gly Gly Ala Ser Thr Leu Leu Ala Leu
           100                 105                 110
Ala His Gln Pro Arg Tyr Val Lys Lys Ala Val Val Ser Ser Phe Ser
       115                 120                 125
Pro Val Ile Asn Glu Pro Met Arg Asp Tyr Leu Asp Arg Gly Cys Gln
   130                 135                 140
```

| | | | | | | | | | | | | | | | |
|---|---|---|---|---|---|---|---|---|---|---|---|---|---|---|---|
| Tyr 145 | Leu | Ala | Ala | Cys | Asp 150 | Arg | Tyr | Gln | Val | Gly 155 | Asn | Leu | Val | Asn | Asp 160 |
| Thr | Ile | Gly | Lys | His 165 | Leu | Pro | Ser | Leu | Phe 170 | Lys | Arg | Phe | Asn | Tyr 175 | Arg |
| His | Val | Ser | Ser 180 | Leu | Asp | Ser | His | Glu 185 | Tyr | Ala | Gln | Met | His 190 | Phe | His |
| Ile | Asn | Gln 195 | Val | Leu | Glu | His | Asp 200 | Leu | Glu | Arg | Ala | Leu 205 | Gln | Gly | Ala |
| Arg | Asn 210 | Ile | Asn | Ile | Pro | Val 215 | Leu | Phe | Ile | Asn | Gly 220 | Glu | Arg | Asp | Glu |
| Tyr 225 | Thr | Thr | Val | Glu | Asp 230 | Ala | Arg | Gln | Phe | Ser 235 | Lys | His | Val | Gly | Arg 240 |
| Ser | Gln | Phe | Ser | Val 245 | Ile | Arg | Asp | Ala | Gly 250 | His | Phe | Leu | Asp | Met 255 | Glu |
| Asn | Lys | Thr | Ala 260 | Cys | Glu | Asn | Thr | Arg 265 | Asn | Val | Met | Leu | Gly 270 | Phe | Leu |
| Lys | Pro | Thr 275 | Val | Arg | Glu | Pro | Arg 280 | Gln | Arg | Tyr | Gln | Pro 285 | Val | Gln | Gln |
| Gly | Gln 290 | His | Ala | Phe | Ala | Ile 295 | | | | | | | | | |

DNA SEQUENCE USEFUL FOR THE PRODUCTION OF POLYHYDROXYALKANOATES

BACKGROUND OF THE INVENTION

1. Field of the Invention

The present invention relates to DNA sequences coding for proteins useful in cell synthesis of polyhydroxyalkanoic acids (PHA). These DNA sequences can be expressed in transformed micro-organisms and plants to produce polyhydroxyalkanoates (PHAs).

2. Description of Related Art

The production of intracellular polyesters belonging to the class of polymers known as polyhydroxyalkanoates (PHAs) has been observed in a wide array of prokaryotic organisms (Anderson and Dawes (1990) *Microbiol. Rev.* 54:450). The monomers composing the polyesters range in length from C4 (3-hydroxybutyrate) to C12 (3-hydroxydodecanoate) (Lageveen et al. (1988) *Appl. Env. Microbiol.* 54:2924). This class of polyesters has attracted much attention as a potential alternative to conventional petrochemical-derived plastics.

PHAs are broadly characterized according to the monomers that constitute their backbone. Polymers composed of C4-C5 units are classified as short chain length (scl) PHAs; polymers containing monomers of C6 units and above are classified as medium chain length (mcl) PHAs. The primary structure of the polymer influences the physical properties of the polyester.

The metabolic pathways leading to the formation of PHAs have not been elucidated for all organisms. The most extensively studied PHA biosynthetic pathway is that of *Alcaligenes eutrophus* (Peoples et al. (1989) *J. Biol. Chem.* 264:15298 and Valentin et. al. (1995) *Eur. J. Biochem.* 227:43). This organism is capable of forming either a homopolymer of C4 (polyhydroxybutyrate, PHB) or a co-polymer of C4-C5 (PHB-PHV, polyhydroxybutyrate-polyhydroxyvalerate) (Koyama and Doi (1995) *Biotechnol. Lett.* 17:281). Hence, *A. eutrophus* is classified as a scl PHA organism. Similarly, Pseudomonas species generate a polymer composed of monomers ranging in length from C6 to C12 (Timm and Steinbüchel (1990) *Appl. Environ. Microbiol.* 56:3360 and Lageveen et al. (1988) *Appl. Environ. Microbiol.* 54:2924), and are classified as mcl PHA organisms.

The polymerization of the hydroxyacyl-CoA substrates is carried out by PHA synthases. The substrate specificity of this class of enzyme varies across the spectrum of PHA producing organisms. This variation in substrate specificity of PHA synthases is supported by indirect evidence observed in heterologous expression studies (Lee et al. (1995) *Appl. Microbiol. Biotechnol.* 42:901 and Timm et al. (1990) *Appl. Microbiol. Biotech.* 33:296). Hence, the structure of the backbone of the polymer is strongly influenced by the PHA synthase responsible for its formation.

Fluorescent pseudomonads belonging to the rRNA homology group I can synthesize and accumulate large amounts of polyhydroxyalkanoic acids (PHA) composed of various saturated and unsaturated hydroxy fatty acids with carbon chain lengths ranging from 6 to 14 carbon atoms (Steinbüchel and Valentin (1992) *FEMS Microbiol. Rev.* 103:217). PHA isolated from these bacteria also contains constituents with functional groups such as branched, halogenated, aromatic or nitrile side-chains (Steinbüchel and Valentin (1995) *FEMS Microbiol Lett.* 128:219). The composition of PHA depends on the PHA polymerase system, the carbon source, and the metabolic routes (Anderson and Dawes (1990) *Microbiol. Rev.* 54:450; Eggink et al. (1992) *FEMS Microbiol. Rev.* 105:759; Huisman et al. (1989) *Appl. Microbiol Biotechnol.* 55:1949; Lenz et al. (1992) *J. Bacteriol.* 176:4385; Steinbüchel and Valentin (1995) *FEMS Microbiol. Lett.* 128:219). In *P. putida*, at least three different metabolic routes occur for the synthesis of 3-hydroxyacyl coenzyme A thioesters, which are the substrates of the PHA synthase (Huijberts et al. (1994) *J. Bacteriol.* 176:1661): (i) β-oxidation is the main pathway when fatty acids are used as carbon source; (ii) De novo fatty acid biosynthesis is the main route during growth on carbon sources which are metabolized to acetyl-CoA, like gluconate, acetate or ethanol; and (iii) Chain elongation reaction, in which acyl-CoA is condensed with acetyl-CoA to the two carbon chain extended 13-keto product which is then reduced to 3-hydroxyacyl-CoA. This latter pathway is involved in PHA-synthesis during growth on hexanoate.

Due to the extended homologies of the primary structures of $PHA_{MCL}$ synthases to the $PHA_{SCL}$ synthases (Steinbüchel et al. (1992) *FEMS Microbiol. Rev.* 103:217), which occur in bacteria accumulating polyhydroxybutyric acid such as, e.g., *Alcaligenes eutrophus*, it seems likely that the substrate of $PHA_{MCL}$ synthases is (R)-3-hydroxyacyl-CoA. The main constituent of the polyester of *P. putida* KT2442 from unrelated substrates such as gluconate is 3-hydroxydecanoate; whereas 3-hydroxyhexanoate, 3-hydroxyoctanoate, 3-hydroxydodecanoate, 3-hydroxydodecenoate, 3-hydroxytetradecanoate, and 3-hydroxytetradecenoate occur as minor constituents (Huijberts et al. (1994) *J. Bacteriol.* 176:1661). Thus, to serve as substrates for the PHA polymerase, the hydroxyacyl residues of the acyl-carrier proteins are most probably converted to the corresponding CoA-derivatives. This can be mediated in a one-step reaction by an (R)-3-hydroxyacyl (ACP to CoA) transferase. Alternatively, the acyl group transfer could be at a different functional group level such as 3-keto or the straight chain. The resulting acyl-CoA would then be converted to the 3-hydroxy level by the action of other enzymes as depicted in FIG. 1. Another possibility, in addition to direct transfer, would be a 2-step process with the release of the free fatty acid by a thioesterase and the subsequent activation to the CoA derivative. This could occur at any level of acyl-ACP as illustrated in FIG. 1.

Elucidation of the protein(s) involved in this conversion is of practical importance because such enzymes are potentially useful in metabolic engineering of recombinant organisms to produce PHAs. For example, expression of (R)-3-hydroxyacyl transferase in the seed of an oil-producing plant (e.g. canola or soybean) would allow transfer of acyl groups directly from lipid synthesis (in which they are ACP-linked) to polymer production (in which they are CoA-linked). Alternatively, a thioesterase and ligase, used consecutively, could accomplish the same reaction.

The isolation of phaG described herein is an example of the isolation of an enzyme that links lipid synthesis to polymer production. The methods employed provide a model for the isolation of such genes in bacteria.

SUMMARY OF THE INVENTION

The present invention provides an isolated DNA fragment comprising a nucleotide sequence encoding a protein that is involved in the linkage between fatty acid biosynthesis and PHA production. This fragment comprises a phaG gene from *Pseudomonas putida* KT2440 that encodes a protein shown to be critical in the production of PHA in *Pseudomonas* putida KT2440 when this organism is grown on a simple carbohydrate substrate (e.g. gluconate). This gene, termed "phaG", and the PhaG protein encoded thereby, as well as biologically functional equivalents thereof, respectively, can be used in conjunction with other PHA biosynthetic enzymes in the production of novel co-polymers of PHA in both prokaryotic and eukaryotic organisms, including plants. Transformed bacteria and transgenic plants comprising and expressing this gene or its equivalents along with other PHA biosynthetic genes such as, but not limited to, a gene encoding a PHA synthase, will be able to form hydroxyacyl-CoA substrates from simple carbon sources via de novo fatty acid synthesis, and thereby produce novel biodegradable polyesters having physical properties similar to those of petrochemical-derived plastics.

The present invention also provides a description of methods that would allow one skilled in the art to isolate, identify, and characterize genes that encode proteins involved in the process of converting lipid biosynthetic intermediates to PHA biosynthetic intermediates. In particular, methods are described for identifying genes that encode CoA-ACP acyltransferases that would be useful in the direct conversion of acyl-ACP to acyl-CoA for PHA biosynthesis.

Further scope of the applicability of the present invention will become apparent from the detailed description provided below. However, it should be understood that the following detailed description and specific examples, while indicating preferred embodiments of the present invention, are given by way of illustration only since various changes and modifications within the spirit and scope of the invention will become apparent to those skilled in the art from this detailed description.

BRIEF DESCRIPTION OF THE DRAWINGS

The above and other objects, features, and advantages of the present invention will be better understood from the following detailed description taken in conjunction with the accompanying The above and other objects, features, and advantages of the present invention will be drawings, all of which are given by way of illustration only and are not limitative of the present invention, in which.

(a) is the partial restriction map of the E3 fragment containing the phaG gene;

(b) shows the restriction subfragments, E3, SF22 and BH13; and (c) shows the position of the structural gene of phaG, with the promoter indicated by an arrow.

SEQ ID NO:1 shows the deduced amino acid sequence of the PhaG protein from P. putida KT2440.

SEQ ID NO:2 shows the nucleotide sequence of fragment E3; the coding strands of the phaG encoding DNA fragment is shown at positions 911 through 1795.

DETAILED DESCRIPTION OF THE INVENTION

The following detailed description of the invention is provided to aid those skilled in the art in practicing the present invention. Even so, the following detailed description should not be construed to unduly limit the present invention as modifications and variations in the embodiments discussed herein can be made by those of ordinary skill in the art without departing from the spirit or scope of the present inventive discovery.

The references cited herein evidence the level of skill in the art to which the present invention pertains. The contents of each of these references, including the references cited therein, are herein incorporated by reference in their entirety.

Figure 1:
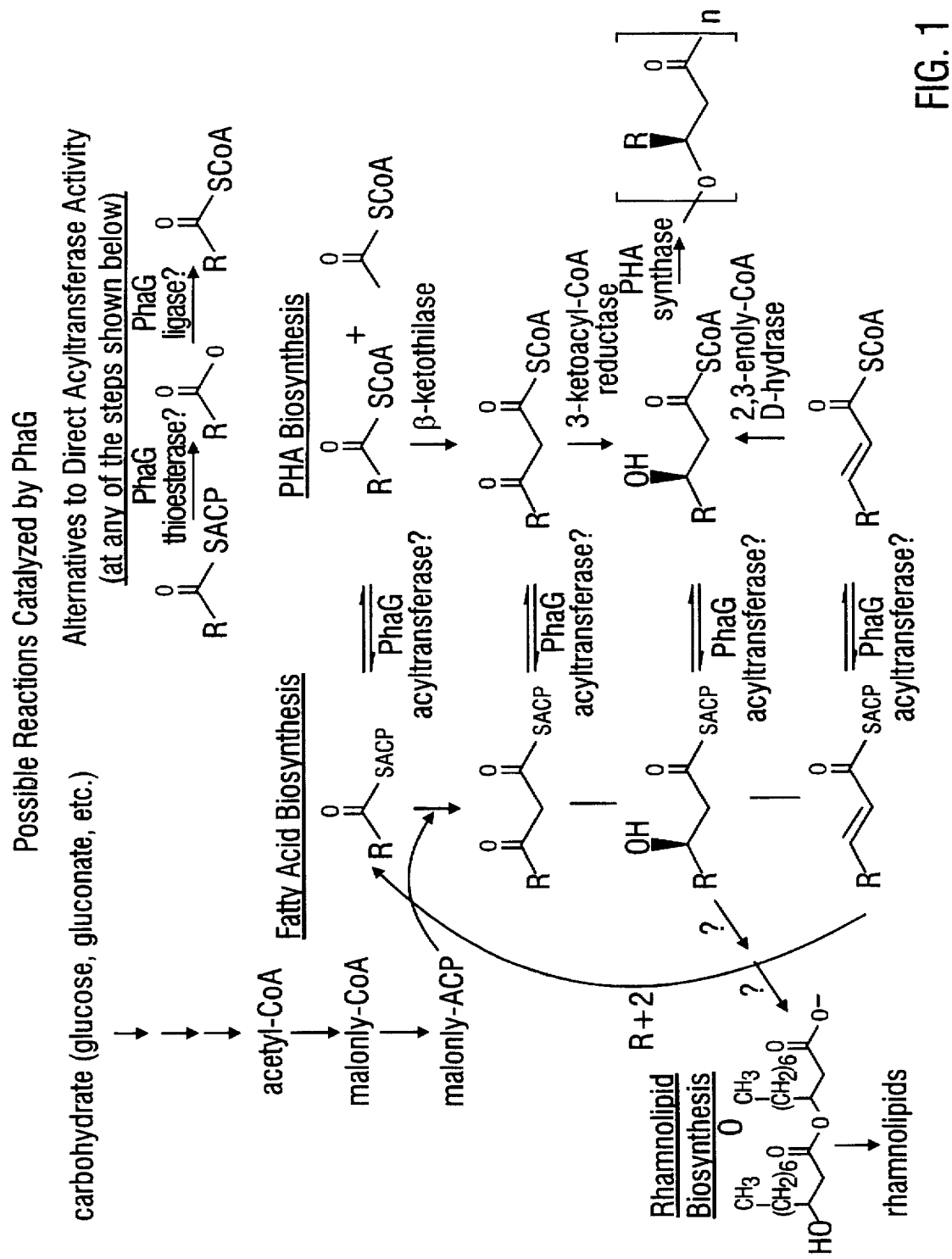
FIG. 1 depicts the possible reactions catalyzed by PhaG during PHA synthesis via de novo fatty acid biosynthesis. The thioesterase/ligase combination could potentially be active on any of the acyl-ACP forms, as is diagrammed in detail for the acyltransferase.

By phenotypical complementation of P. putida KT2440 $PHAG_N$ 195 mutants which are defective exclusively in the branch of PHA biosynthesis occurring via de novo fatty acid biosynthesis, we identified and characterized phaG as a new gene locus relevant for PHA biosynthesis in P. putida. The PHA synthetic pathway via the β-oxidation was not affected in the $PHAG_N$ mutants. $PHAG_N$ mutants were not complemented with the PHA-synthase locus of P. aeruginosa PAOI and the adjacent genomic region. In contrast, mutants of P. putida KT2440 which were completely impaired in the PHA synthesis on either substrate were complemented by the PHA synthase locus of P. aeruginosa. Therefore, $PHAG_N$ mutants are not defective in the PHA-synthase locus, and most probably phaG is not closely linked to the PHA synthase locus. Furthermore, phaG is not in general essential for the synthesis of PHA in P. putida KT2440, but is only required for PHA synthesis and accumulation from gluconate or other simple carbon sources (e.g., glucose, sucrose, fructose or lactose), which are catabolized to acetyl-CoA in this organism before PHA synthesis starts. FIG. 1 depicts the possible reactions catalyzed by PhaG, any of which, if impaired, could account for the mutant phenotype.

From the results of labeling studies, nuclear magnetic resonance spectroscopy (NMR) and gas chromatography-mass spectroscopy (GC-MS) Eggink et al. (1992) FEMS Microbiol. Rev. 105:759 and Huijberts et al. (1992) Appl. Environ. Microbiol. 58:536 and (1994) J. Bacteriol. 176:1661 concluded that the precursors of PHA biosynthesis from simple carbon sources are predominantly derived from (R)-3-hydroxyacyl-ACP intermediates occurring during the de novo fatty acid biosynthetic route. Since the constituents of PHB and PHA are in the R-configuration, and since $PHA_{SCL}$- and $PHA_{MCL}$-synthases are highly homologous, the intermediates in fatty acid metabolism are likely converted to (R)-3-hydroxyacyl-CoA before polymerization. Nevertheless, some other routes of PHA synthesis are also possible. At present it cannot be excluded that (R)-3-hydroxyacyl-ACP thioesters are direct substrates for PHA synthases. Another conceivable alternative is the release of free fatty acids by the activity of a thioesterase. A ligase may subsequently activate those fatty acids to the corresponding hydroxyacyl-CoA thioesters. In addition, it is conceivable that the acyl transfer link from ACP to CoA is not at the 3-hydroxy thioester level, but at another acyl functional group level as depicted in FIG. 1.

Mutagenesis of P. putida KT 2440 did not yield mutants that were completely impaired in the biosynthesis of PHA from gluconate. We identified five mutants which accumulated PHA only up to 3% of the cellular dry weight (CDW) (which were referred to as subclass I mutants), as well as three mutants, which accumulated 5 to 16% of CDW when grown on gluconate (subclass II). All mutants contained monomer composition of the polyester typical for this pathway, as far as was detectable. However, the analysis of the generated mutants, the complementation studies, and the genomic organization of phaG revealed no indication for the existence of another protein essential for the PHA synthesis from simple carbon sources in *P. putida* KT 2440. Therefore, there may be only one additional specific enzymatic step required for PHA synthesis from gluconate that is not required for PHA synthesis from octanoate. Weak PHA accumulation by subclass I mutants provides evidence for the existence of a pathway mentioned above, which acts in parallel to the PhaG dependent route with very low efficiency. The relatively larger amount of PHA accumulated by subclass II mutants might be a result of leaky mutations leaving the phaG gene product partially active.

The high degree of homology of phaG to rhlA and the qin region of *P. aeruginosa*, respectively, indicates a function similar to that of these proteins. The exact function of the "quinolone sensitivity protein" has not yet been described. Quinolones such as nalidixic acid are synthetic antibiotics exhibiting strong antimicrobial effects on Gram-negative bacteria including *P. aeruginosa*. The rhlA gene product is involved in the rhamnolipid biosynthesis of *P. aeruginosa* PG201. *P. aeruginosa* rhamnolipid biosurfactants are synthesized during the late-exponential and stationary growth phases. Rhamnolipid biosynthesis proceeds by sequential glycosyl transfer reactions, each catalyzed by specific rhamnosyltransferases with TDP-rhamnose acting as a rhamnosyl donor and 3-hydroxydecanoyl-3-hydroxydecanoate or L-rhamnosyl-3-hydroxydecanoyl3-hydroxydecanoate acting as acceptors as proposed by Burger et al. (1963) *J. Biol. Chem.* 238:2595 and (1966) *Methods Enzymol.* 8:441. 3-hydroxydecanoate can be formed via β-oxidation or via fatty acid biosynthesis (Boulton and Ratledge (1987) *Biosurfactants and Biotechnology* p. 47). A dimer consisting of two 3-hydroxydecanoic acid molecules is formed by condensation, however the exact mechanism of this step is not known. RhlA significantly enhanced the level of rhamnolipids in rhamnolipid negative mutants of *P. aeruginosa* PG201 when it was coexpressed with the rhamnosyltransferase (RhlB) compared with the expression of the isolated rhlB gene. Amino acid analysis revealed a putative signal peptide for the N terminus of RhlA. From these results, Ochsner et al. (1994) *J. Biol. Chem.* 269:19787 suggested that the RhlR protein is involved in the synthesis or in the transport of rhamnosyltransferase precursor substrates or that RhlA is necessary for the stability of the RhlB protein in the cytoplasmic membrane. The N-terminal region of PhaG shares also some characteristics with signal peptides found in Gram-negative bacteria, like the polar N-domain, the hydrophobic H-domain and the less hydrophobic C-domain, but it lacks the typical second turn and a putative leader peptidase cleavage site in the C-domain. Due to the cryptic leader sequence PhaG might have originally been involved in another pathway but may have changed its function during the evolution of the organism.

3-Hydroxyacyl-ACP intermediates provided by fatty acid biosynthesis are presumably the common intermediates of both the PHA and the rhamnolipid biosynthesis pathways from gluconate. If the ACP derivatives do not themselves serve as substrates for PHA synthases or the enzymes involved in rhamnolipid synthesis for the condensation of two 3-hydroxydecanoyl-moieties, they must be either directly transesterified to the corresponding CoA derivatives or are transferred to CoA thioesters by the combined action of a thioesterase and a ligase. With reference to FIG. 1, therefore, PhaG may be a (R)-3-hydroxyacyl CoA-ACP acyltransferase catalyzing the conversion of (R)-3-hydroxyacyl-ACP to (R)-3-hydroxyacyl-CoA derivatives, which serve as ultimate precursors for the PHA polymerization from unrelated substrates in Pseudomonads as it was proposed by Eggink et al. (1992) *FEMS Microbiol. Rev.* 105:759 and van der Leij and Witholt (1995) *Can. J. Microbiol.* 41, Supp. 1:22. Alternatively, PhaG may be a CoA-ACP acyltransferase with an acyl group specificity other than the 3-hydroxy functionality mentioned above, or have activity associated with a specific thioesterase or ligase (refer to FIG. 1). In addition, instead of being a catalytic enzyme, PhaG may be a protein that stabilizes or regulates a catalytic protein complex which catalyzes the acyl group transfer reaction or thioesterase or ligase activity.

Definitions

The following definitions are provided in order to aid those skilled in the art in understanding the detailed description of the present invention.

"ACP" refers to acyl carrier protein.

"CoA" refers to coenzyme A.

"CoA-ACP acyltransferase" or "acyltransferase" refers to an enzyme that catalyzes acyl group transfer between ACP and CoA.

"C-terminal region" refers to the region of a peptide, polypeptide, or protein chain from the middle thereof to the end that carries the amino acid having a free carboxyl group.

The phrase "DNA segment heterologous to the promoter region" means that the coding DNA segment does not exist in nature in the same gene with the promoter to which it is now attached.

The term "encoding DNA" refers to chromosomal DNA, plasmid DNA, cDNA, or synthetic DNA which encodes any of the enzymes discussed herein.

The term "genome" as it applies to bacteria encompasses both the chromosome and plasmids within a bacterial host cell. Encoding DNAs of the present invention introduced into bacterial host cells can therefore be either chromosomally-integrated or plasmid-localized. The term "genome" as it applies to plant cells encompasses not only chromosomal DNA found within the nucleus, but organelle DNA found within subcellular components of the cell. DNAs of the present invention introduced into plant cells can therefore be either chromosomally-integrated or organelle-localized.

"Ligase" refers to an enzyme that catalyzes the activation of a free fatty acid to the CoA thioester.

The terms "microbe" or "microorganism" refer to algae, bacteria, fungi, and protozoa.

The term "mutein" refers to a mutant form of a peptide, polypeptide, or protein.

"N-terminal region" refers to the region of a peptide, polypeptide, or protein chain from the amino acid having a free amino group to the middle of the chain.

"Overexpression" refers to the expression of a polypeptide or protein encoded by a DNA introduced into a host cell, wherein said polypeptide or protein is either not normally present in the host cell, or wherein said polypeptide or protein is present in said host cell at a higher level than that normally expressed from the endogenous gene encoding said polypeptide or protein.

The term "plastid" refers to the class of plant cell organelles that includes amyloplasts, chloroplasts, chromoplasts, elaioplasts, eoplasts, etioplasts, leucoplasts, and proplastids. These organelles are self-replicating, and contain what is commonly referred to as the "chloroplast genome," a circular DNA molecule that ranges in size from about 120 to about 217 kb, depending upon the plant species, and which usually contains an inverted repeat region.

The phrases "PHA biosynthetic genes" and "PHA biosynthetic enzymes" refer to those genes or enzymes leading to anabolic reactions in the pathway of PHA production.

The phrase "polyhydroxyalkanoate (PHA) synthase" refers to enzymes that convert hydroxyacyl-CoAs to polyhydroxyalkanoates and free CoA.

The phrase "simple carbohydrate substrate" means a mono- or oligosaccharide but not a polysaccharide; simple carbohydrate substrate includes glucose, fructose, sucrose, lactose. More complex carbohydrate substrate commonly used in media such as corn syrup, starch, and molasses can be broken down to simple carbohydrate substrate.

"Thioesterase" refers to an enzyme that catalyzes the hydrolysis of acyl-ACP groups to the free fatty acid plus ACP.

Materials and Methods

Growth of bacteria. *E. coli* was grown at 37° C. in Luria-Bertani (LB) medium. Pseudomonads were grown at 30° C. either in a complex medium of nutrient broth (NB; 0.8%, wt/vol) or in a mineral salts medium (MM) (Schlegel et al. (1961) *Arch. Mikrobiol.* 38:209) with 0.05% (w/v) ammonia.

Polyester analysis. To determine the polyester content of the bacteria, 3–5 mg lyophilized cell material was subjected to methanolysis in the presence of 15% (v/v) sulfuric acid. The resulting methyl esters of the constituent 3-hydroxyalkanoic acids were assayed by gas chromatography (GC) according to Brandt et al. (1988) *Appl. Environ. Microbiol.* 54:1977 and as described in detail recently (Timm and Steinbüchel (1990)*Appl. Environ. Microbiol.* 56:3360).

Isolation of RNA and DNA. Total RNA was isolated as described by Oelmüller et al. (1990) *J. Microbiol. Meth.* 11:73. Plasmid DNA was prepared from crude lysates by the alkaline extraction procedure (Birnboim and Doly (1979) *Nucl. Acids Res.* 7:1513). Total genomic DNA was isolated according to Ausubel et al. (1987) *Current Protocols in Molecular Biology*, John Wiley & Sons, NY, USA.

Analysis and manipulation of DNA. Isolated plasmid DNA was digested with various restriction endonucleases under the conditions described by Sambrook et al. (1989) *Molecular Cloning. A Laboratory Manual*, 2nd Ed., Cold Spring Harbor Laboratory Press, Cold Spring Harbor, N.Y. or by the manufacturer. DNA restriction fragments were isolated from agarose gels by using the Geneclean kit (Vogelstein, B. and D. Gillespie (1979) *Proc. Natl. Acad Sci. USA* 76:615).

Transfer of DNA. For transformation, *E. coli* was grown aerobically in LB medium containing 20 mM $MgCl_2$ at 37° C. Competent cells were prepared and transformed by using the calcium chloride procedure described by Sambrook et al. (1989) *Molecular Cloning. A Laboratory Manual*, 2nd Ed., Cold Spring Harbor Laboratory Press, Cold Spring Harbor, N.Y. Mating of *P. putida* KT2440 mutants (recipients) with *E. coli* S 17-1 (donor) harboring hybrid donor plasmids were performed by "minicomplementation". 300 µl of a concentrated recipient cell suspension ($OD_{436nm}$=100) were spread onto MM-medium agar plates supplemented with 1.5% gluconate or 0.3% octanoate plus 25 mg tetracycline per 1. After 5 min incubation cells of 50 different donor strains were transferred with toothpicks from colonies to each agar plate containing a layer of the recipient. The plates were incubated at 30° C. for 36 hours.

Synthesis of oligonucleotides. Synthetic oligonucleotides were synthesized in 0.2 µmol portions from deoxynucleoside phosphoamidites (Beaucage and Caruthers (1981) *Tetrahedron Lett.* 22:1859) in a Gene Assembler Plus apparatus according to the protocol provided by the manufacturer (Pharmacia-LKB, Uppsala, Sweden). Oligonucleotides were released from the support matrix, and the protection groups were removed by 15 h incubation at 55° C. in 25% (vol/vol) ammonia. Oligonucleotides were finally purified by passage through a NAP-5 column (Pharmacia-LKB, Uppsala, Sweden).

DNA sequence analysis. DNA sequencing was carried out by the dideoxy-chain termination method according to Sanger et al. (1977) *Proc. Natl Acad Sci. USA* 74:5463 with single stranded or with double stranded alkali denatured plasmid DNA, but with 7-deazaguanosine 5'-triphosphate instead of dGTP (Mizusawa, S. et al. (1986) *Nucl. Acids Res.* 14:1319), and with [$\alpha^{35}S$]-dATP using a T7-polymerase sequencing kit according to the manufacturers protocol (Pharmacia-LKB, Uppsala, Sweden). Synthetic oligonucleotides were used as primers and the "primer-hopping strategy" (Strauss, E. C. et al. (1986) *Anal. Biochem.* 154:353) was employed. Products of the sequencing reactions were separated in 8% (wt/vol) acrylamine gels in buffer (pH 8.3) containing 100 mM hydrochloride, 83 mM boric acid, 1 mM EDTA and 42% (wt/vol) urea in a S2-sequencing apparatus (GIBCO/BRL Bethesda Research Laboratories GmbH, Eggenstein, Germany) and were visualized on X-ray films.

Analysis of sequence data. Nucleic acid sequence data and deduced amino acid sequences were analyzed with the Sequence Analysis Software Package (Version 6.2, June 1990) according to Devereux et al. (1984) *Nucl. Acids Res.* 12:387.

Determination of the transcriptional start site. The determination of the transcriptional start site was done by a nuclease protection assay. The hybridization conditions for the S1 nuclease protection assays were done as described in detail by Berk and Sharp (1977) *Cell* 12:721 and Sambrook et al. (1989) *Molecular Cloning: A Laboratory Manual*, 2nd Ed., Cold Spring Harbor Laboratory Press, Cold Spring Harbor, N.Y., and the S1 nuclease reactions were conducted by the method described by Aldea et al. (1988) *Gene* 65:101. DNA probes and dideoxynucleotide sequencing reactions for sizing the signals were performed with pBluescript SK-BH13 DNA (Tab. 1, and FIG. 1) as a template. In the annealing reaction, the oligonucleotide (5'-GGGTATTCGCGTCACCT-3'), which was complementary to positions 887 to 871, and the oligonucleotide 5'-CCGCATCCGCGCGATAG-3', which was complementary to positions 986 to 970, respectively, were used for [$^{35}S$] labeling. For all mapping experiments, 25 µg of RNA was mixed with the labeled DNA fragments; the specific labeling rate was higher than $10^7$ cpm/µg of DNA.

Polymerase chain reaction (PCR). PCR amplifications were performed in 100-µl volumes according to Sambrook et al. (1989) *Molecular Cloning: A Laboratory Manual*, 2nd Ed., Cold Spring Harbor Laboratory Press, Cold Spring Harbor, N.Y. by a Omnigene thermocycler (Hybaid Ltd., Teddington, U.K.) and the Vent-polymerase (New England Biolabs GmbH, Schwalbach, Germany). The following heterologous primers (in 5'- to 3'-direction) were used for site directed mutagenesis: TTTGCGCCAGGATCCGAT-CATATGAGGCCAGAAATC containing artificial BamHI and NdeI sites, and GTTATAAAAAAGCTTTGTCGGCG harboring the native HindIII site downstream of phaG.

Preparation of cell extracts. Approximately 1 g (wet weight) of *E. coli* cells were suspended in 1 ml of buffer A (50 mM Tris hydrochloride; pH 7.4, 0.8% (vol/vol) Triton-X 100, 10 mM magnesium chloride, 10 mM EDTA which was supplemented with 200 µg of phenylmethylsulfonyl fluoride per ml), and disrupted by sonification for 1 min at an amplitude of 14 µm in a W 250 sonifier (Branson Schallkraft GmbH, Germany). Soluble cell fractions were obtained as supernatants from 30 min of centrifugation at 50,000 x g and 4° C.

Electrophoretical methods. Sodium dodecyl sulfate (SDS)- and mercaptoethanol-denatured proteins were separated in 11.5% (wt/vol) polyacrylamine gels in Tris-glycine buffer (25 mM Tris, 190 mM glycine, 0.1% (wt/vol) SDS (Laemmli, 1970). Proteins were stained with Coomassie brilliant blue (Weber, and Osborn, 1969).

Chemicals. Restriction endonucleases, the DNA detection kit, RNA molecular weight markers, T4 DNA ligase, and DNA modifying enzymes were obtained from Lifetechnologies GmbH (Eggenstein, Germany). RNase-free DNase, agarose NA, and phosphoamidites were from Pharmacia-LKB (Uppsala, Sweden). Formaldehyde was from Sigma Chemical Co. (Gauting, Germany); whereas formamide, ethidium bromide, and EDTA were from Serva Feinbiochemica GmbH & Co. (Heidelberg, Germany). Complex media were from Difco Laboratories (Detroit, USA). All other chemicals were of the highest purity available from E. Merck AG (Darmstadt, Germany).

EXAMPLE 1

Isolation of mutants defective in PHA synthesis via de novo fatty acid biosynthesis To obtain mutants of P. putida KT 2440 affected in PHA metabolism, nitrosoguanidine mutagenesis was performed according to Miller et al. (1972). Cells were incubated for 15 min. in the presence of 200 µg N-methyl-N'-nitro-N-nitrosoguanidine per ml. Appropriate dilutions of cell suspensions were plated on mineral salts medium (MM)-agar plates containing 0.05% (w/v) ammonia and 1.5% (w/v) sodium gluconate as sole carbon source. Cells accumulating PHA were distinguished from cells of mutants not accumulating PHA due to differences in the opacity of the colonies. To distinguish between mutants which were defective in the PHA synthase locus and did not synthesize PHA from either substrate, and mutants which were only defective in the PHA synthesis via de novo fatty acid biosynthesis, cells from transparent colonies were also transferred from MM-gluconate plates to MM-agar plates containing 0.3% sodium octanoate. Mutants, which formed transparent colonies on gluconate agar plates but opaque colonies on octanoate agar plates were referred to as $PHAG_N$ phenotype mutants. They were grown in liquid cultures for two days, and the cells were subject to gas chromatography to analyze the content and composition of PHA. We identified five mutants which accumulated PHA only up to 3% of the cellular dry weight (CDW) (which were referred to as subclass I mutants), as well as three mutants, which accumulated 5 to 16% of CDW when grown on gluconate (subclass II). See Table 1. Representatives of both subclasses accumulated normal amounts of PHA (up to 85% of CDW) when cultivated on octanoate as the sole carbon source. The composition of the polymer, so far detectable, was not affected. Cell growth of these mutants on octanoate or on gluconate was not affected and occurred at the same rate as for the wild type. In addition to these mutants, we obtained two mutants which were impaired in the synthesis of PHA from gluconate as well as from octanoate. (see Table 1). These mutants therefore exhibited the same phenotype as the mutant P. putida GpP104 which was isolated previously (Huisman et al. (1992) Appl. Environ. Microbiol. 58:536).

Although chemical mutagenesis was used herein, a number of additional chemical, biological, and physical methods for generating mutants (for example, other mutagenic chemicals, transposons, or UV light) will be obvious to those skilled in the art.

TABLE 1

Bacterial strains plasmids, bacteriophage and DNA-fragments used in this study.

| Stains and plasmids | Relevant characteristics | Source of reference |
|---|---|---|
| *Pseudomonas putida* | | |
| KT2440 | mt-2, hsdR1(r⁻m+), ohne TOL-plasmid | (Worsey and Williams (1975) J Bacteriol. 124:7) |
| NK2:1 | P. putida KT2440 mutants | This study |
| NK2:2 | defective PHA synthesis from | This study |
| NK:9 | simple carbon sources | This study |
| NK:18 | (mutant type $PHAG_{NI}$) | This study |
| NK3:2 | | This study |
| NK1:30 | P. putida KT2440 mutants | This study |
| NK2:56 | defective in PHA synthesis from simple carbon sources (mutant type $PHAG_{NII}$) | This study |
| NK:17 | | This study |
| NK2:3 | P. putida KT2440 mutants | This study |
| NK2:8 | impaired in PHA biosynthesis | This study |
| *Escherichia coli* | | |
| BL21(DE3) | hsdSgal(lc1ts857 ind1Sam7 nin5 lacUV5-T7 gene1) | (Studier and Moffatt (1986) J. Mol. Biol. 189:113) |
| S17-1 | recA; harbors the tra genes of plasmid RP4 in the chromosome; proA, thi-1 | (Simon et al. (1983) Biotechnology 1:784) |
| XL1-Blue | recA1 endA1 gyrA96 thi hsdR17 (rk⁻, mk⁺) supE44 relA1, λ-, lac [F' proAB lacIqZVM15, Tn10(Tet)] | (Bullock et al. (1987) Bio Techniques 5:376) |
| pVK100 | Tc', Km', broad host range cosmid | (Knauf and Nester (1982) Plasmid8:45) |
| pVK100:K18 | pVK100 harboring three genomic EcoRI fragments of P. putida KT2440. Harbors phaG | This study |

TABLE 1-continued

Bacterial strains plasmids, bacteriophage and DNA-fragments used in this study.

| Stains and plasmids | Relevant characteristics | Source of reference |
|---|---|---|
| pMP92 | Tc$^r$, broad host range plasmid | (Spaink et al. (1987) Plant Mol. Biol. 9:27) |
| pMPE3 | pMP92 containing the 3-kbp E3 fragment harboring phaG | This study |
| pMPBH13 | pMP92 containing the 1.3 kbp BamHI-HindIII subfragment of E3 harboring phaG including the promoter | This study |
| pMPSE22 | pMP92 containing the 2.2 kbp SalI-EcoRI subfragment of E3 harboring phaG without promoter | This study |
| pBluescript SK- | Ap$^r$, lacPOZ', T7 and T3 promoter | Stratagene |
| pT7-7 | φ10 promoter, Ap$^r$ | (Tabor and Richardson (1991) Proc. Natl. Acad. Sci. U.S.A. 82:1074) |
| pT7-G1 | pT7-7 harboring phaG | This study |

EXAMPLE 2

Complementation of mutants affected in the PHA synthesis via the de novo fatty acid biosynthesis We constructed a library of EcoRI digested *P. putida* KT2440 genomic DNA with the cosmid vector pVK100 (Knauf and Nester (1982) *Plasmid* 8:45) and the Gigapack II Gold Packaging Extract (Stratagene Cloning Systems, La Jolla, Calif.) in *E. coli* S17-1. Approximately 5,000 transductants were applied to minicomplementation experiments, with the PHAG$_{NI}$ type mutant 2:1 as the recipient. Phenotypic complementation could be observed after two days of incubation at 30° C. on MM-agar plates supplemented with 1.5% gluconate by the opacity of the transductant colonies. One of the hybrid cosmids (pVK100::K18) harbored three EcoRI-fragments (3, 6, and 9 kbp) and enabled the PHAG$_{NI}$ mutants to accumulate PHA again from carbon sources catabolized via acetyl-CoA. Subcloning of these fragments to the EcoRI digested broad host range vector pMP92 (Spaink et al. (1987) *Plant Mol. Biol.* 9:27) and the subsequent conjugational transfer to the mutant 2:1 showed that the 3-kbp EcoRI-fragment was responsible for the complementation. This fragment was designated as E3 (FIG. 2), and it complemented any of the eight isolated mutants exhibiting this phenotype. Complementation was not achieved by the hybrid cosmid pHP1016::PP2000 comprising the entire 7.3-kbp PHA synthase locus of *Pseudomonas aeruginosa* PAO1 plus approximately 13kbp of the upstream region of this locus or by the hybrid cosmid pHP1016::PP180 comprising the phaC2 gene of *P. aeruginosa* PAO1 plus approximately 16 kbp of the adjacent downstream region (Timm and Steinbuüchel (1992) *Eur. J Biochem.* 209:15). Both mutants from this study which were completely impaired in the PHA synthesis were complemented with the pHP1016::PP2000 hybrid cosmid, but were not complemented with the pPH1016::PP180 construct, which lacked a functional promoter upstream of the phaC2 gene, or with plasmid pVK100::K18.

Mutant NK 2:1, harboring a plasmid containing the E3 fragment, was deposited with Deutsche Sammiung Von Mikroorganismen und ZellKulturen GmbH (DSM), Mascheroder Weg 1b, D-3300 Braunschweig, Germany, on Apr. 12, 1995 as deposit no. DSMZ 9922.

EXAMPLE 3

Additional methods for cloning acyltransferase, thioesterase, and acyl-CoA ligase genes.

The isolation of phaG mutants and cloning of phaG by complementation, described in examples 1 and 2, supra, provide a method for detecting genes involved in the transfer of carbon compounds from lipid biosynthesis to PHA biosynthesis. Those skilled in the art will recognize additional methods to clone genes involved in this process. Such methods include a combination of biochemical, genetic, and molecular cloning approaches.

i. Development of enzymatic assays for acyltransferase, thioesterase, and acyl-CoA ligase activities will provide new methods for cloning the encoding genes.

There are a number of ways to probe for CoA-ACP acyltransferase activity. One method is to analyze the acylation of ACP using acyl-CoA as the starting substrate, and identify the acyl-ACP product with urea-polyacrylamide gel electrophoresis (urea-PAGE). Urea-PAGE has been demonstrated to be useful for resolving ACP pool composition (Post-Beittenmiller et al. (1991) *J Biol. Chem.* 266:1858; Keating et al. (1996) *J. Bacteriol.* 178:2662). Detection on the gel is by coomassie staining, or, if the starting acyl-CoA is radiolabeled in the acyl group, detection is by autoradiography. Alternatively, if one uses acyl-radiolabeled acyl-CoA or acyl-ACP as starting substrate, a high throughput screen can be performed in a 96-well format. In this case, acyl-ACP is selectively precipitated with aqueous trichloroacetic acid (Kopka et al. (1995) *Anal. Biochem.* 224:51), separated using a commercially available 96-well filter plate, washed, and radioactivity in the various compartments is quantitated. Acyl-CoA and CoA are captured in the eluate capture plate, while precipitated ACP and acyl-ACP are trapped in the filter. Counting is done using any commercially available plate counter. The above methods should work equally well with acyl groups of various composition. That is, with a straight chain, 2,3-enoyl-, 3-hydroxy-, or 3-keto- functionality.

An acyltransferase spectroscopic assay, performed in 96-well plates if desired, could be designed to monitor acyl-ACP conversion to acyl-CoA by an enzymatic coupling system that would vary depending on the acyl group functionality. For example, if the acyl group is 3-hydroxy, one could detect the formation of 3-hydroxyacyl-CoA by coupling to 3-hydroxyacyl-CoA dehydrogenase and monitoring the conversion of $NAD^+$ to NADH at 340 nm. A 3-keto functionality could be monitored in the same manner, but in the reverse direction. Similar, but extended coupling schemes could be designed for straight chain, or 2,3-enoyl acyl groups leading in the end to the 3-hydroxyacyl-CoA dehydrogenase and $NAD^+$ or NADH for detection.

The function of a ligase is to activate a free fatty acid to the CoA thioester level, typically using a nucleotide triphosphate (NTP) as the chemical activating agent. In this process NTP is converted to pyrophosphate (PPi) and nucleotide monophosphate (NMP). One could design an assay to detect ligase activity that is similar to that described for acyltransferase. That is, the acyl-CoA product formed (whether it is a straight chain, 2,3enoyl-, 3-hydroxy-, or 3-keto- functionality), could be coupled directly, or with an extended coupling system, to the 3-hydroxyacyl-CoA dehydrogenase. Detection would again be spectrophotometric, monitoring NADH production or consumption at 340 nm. Alternatively, if the ligase indeed utilizes an NTP as the activating agent, then one could analyze for PPi following its conversion to free phosphate using inorganic pyrophosphatase. Free phosphate can be quantitated using standard phosphate-based assays.

The hydrolysis of an acyl-ACP by a thioesterase to form the free fatty acid and free ACP could be detected in a 96-well format using radiolabeled acyl-ACP and the filter plate technology described above. In this particular case, however, one would monitor for the appearance of free radiolabeled fatty acid in the eluent capture plate, or the remaining, unhydrolyzed radiolabeled acyl-ACP in its precipitated form in the filter plate. Another possible assay amenable to a 96-well format would be to detect the sulfhydryl from the phosphopantetheine group in free ACP with Ellman's reagent, 5,5'dithio-bis(2-nitrobenzoic acid) (DTNB). This reagent will react with free sulfhydryls, producing a strong yellow color with an extinction coefficient of $13.6$ $mM^{-1}$ $cm^{-1}$ (Ellman, 1959).

ii. Using an enzymatic assay as a means to purify the enzyme allows isolation of the gene using information gained from the protein sequence. Once pure, the protein is digested with protease and fragments purified. Various fragments are sequenced using standard techniques and degenerate oligonucleotide probes produced based on the protein sequence (Sambrook et al. (1989) *Molecular Cloning: A Laboratory Manual*, 2nd Ed., Cold Spring Harbor Laboratory Press, Cold Spring Harbor, N.Y.). These probes are hybridized to a genomic library produced from the organism of interest (Sambrook et al. (1989) *Molecular Cloning: A Laboratory Manual*, 2nd Ed., Cold Spring Harbor Laboratory Press, Cold Spring Harbor, N.Y.). Clones that hybridize to the probes are sequenced and the amino acid sequence predicted from the DNA is compared to that determined from the protein in order to verify cloning of the correct gene.

iii. Detection of enzymatic activity in a bacterial lysate allows screening of randomly-generated mutants for those lacking the activity. Mutants are generated by any of the means described above and several thousand clones from each mutagenesis reaction are screened for the appropriate enzymatic activity. Alternatively, mutants can be screened for the absence of an enzyme using antibodies generated against the purified protein (Sambrook et al. (1989) *Molecular Cloning: A Laboratory Manual*, 2nd Ed., Cold Spring Harbor Laboratory Press, Cold Spring Harbor, N.Y.). Any mutants identified in these screens are complemented as described above in order to identify the acyltransferase gene.

iv. Any enzyme, or combination of enzymes, that converts β-hydroxyacyl-ACP to β-hydroxyacyl-CoA could potentially be cloned by transforming a PHA-negative bacterium, harboring only a PHA synthase, with a genomic library constructed from an organism suspected to have the desired activity. The β-hydroxyacyl-CoA could be used directly as a substrate for PHA synthesis by the PHA polymerase, thus allowing screening for production of PHA from a simple carbon source as described supra. Any strain making PHA would then be checked to determine if PHA synthesis is due to cloning of an acyltransferase, a thioesterase plus ligase, or β-ketothiolase plus acyl-CoA reductase.

v. The gene encoding the desired activity can be identified using expression libraries of DNA from the organism of interest cloned into plasmid or λ phage harbored in *E. coli* (Sambrook et al. (1989) *Molecular Cloning: A Laboratory Manual*, 2nd Ed., Cold Spring Harbor Laboratory Press, Cold Spring Harbor, N.Y.). Expressed proteins from cloned genes are assayed either using direct enzymatic assay of clones, or by screening the clones using antibodies generated against the purified protein. Clones identified as encoding acyltransferase, thioesterase, or ligase are restriction mapped and subcloned to identify the relevant gene, the gene is sequenced, and the amino acid sequence predicted by the gene is compared to that derived from sequencing of the purified protein.

vi. Expression of phaG is dependent upon whether the cells are grown on gluconate or fatty acids (see Example 6), and similar regulation of any protein involved in transfer of acyl group from ACP to CoA might be expected since its activity would only be required when synthesizing PHA from simple carbon sources. Genes that are differentially expressed can be cloned using subtractive cDNA probes (Sambrook et al. (1989) *Molecular Cloning: A Laboratory Manual*, 2nd Ed., Cold Spring Harbor Laboratory Press, Cold Spring Harbor, N.Y.) or by direct cloning of the cDNAs following the subtraction procedure (Kim et al. (1993) *J. Mol. Biol.* 231:960). Priming of cDNA synthesis can be achieved using oligo -dT primers to anneal to poly-A tails on the mRNA. Poly-A tails are present on at least a subset of mRNA molecules in a number of prokaryotes, and bacterial cDNA libraries have been produced using oligo-dT primers (Kushner (1996) *ASM Press*, Washington, D.C. p. 849; Kim et al. (1993) *J. Mol. Biol.* 231:960; Gopalakrishna and Sakar (1982) *J. Biol. Chem.* 257:2747). An alternative priming strategy utilizes random oligonucleotides for priming of cDNA synthesis (Kim et al. (1993) *J. Mol. Biol.* 231:960). Following the cDNA subtraction procedure, the probes are used in hybridization screens to identify clones from a genomic library of the organism of interest. Alternatively, the cDNA's are cloned directly. Clones identified in this screen are sequenced and compared to genes encoding various known acyltransferases and phaG in order to identify potential acyltransferases. These clones can also be used as probes to indentify genomic clones containing the entire gene that encodes the mRNA from which the cDNA was generated. Additionally, the randomly-primed cDNA's (which are unlikely to encode an entire gene) can be cloned into a suicide vector (e.g., that used by Lenz et al. (1994) *J. Bacteriol.* 176:4385), integrated into the genome of the source organism to produce mutants, and the mutants are analyzed for their ability to produce PHA from simple carbon sources. Any mutants affected in PHA synthesis can be complemented using genomic clones of the organism of interest, as described in example 2, supra.

vii. Differentially-expressed proteins can be detected directly using 2-dimensional polyacrylamide gel electrophoresis. This approach has been successfully utilized by Neidhardt and coworkers to study proteins under regulon control in *E. coli* (e.g., VanBogelen et al. (1996) *J. Bacteriol.* 178:4344). Proteins identified as being differentially regulated according to carbon source can be purified and sequenced, and the gene(s) encoding them cloned and analyzed as described above.

EXAMPLE 4

Determination of the gene locus and nucleotide sequence of phaG

The 3-kbp E3 fragment (FIG. 2) was cloned to the pBluescript SK- vector, and the nucleotide sequence was determined by the dideoxy-chain termination method and the primer-hopping strategy by employing universal, reverse and synthetic oligonucleotides as primers. SEQUENCE LISTING SEQ ID NO:1 shows the nucleotide sequence of fragment E3. This fragment comprised 3.061 nucleotides with three ORF's. ORFI and ORF3 are localized only incompletely on this fragment with ORFI lacking the 5'-region and with ORF3 lacking the 3'-region. See FIG. 2. The amino acid deduced from ORFI revealed significant homologies to a hypothetical, uncharacterized protein of *Haemophilus influenzae* (Fleischmann, R. D. et al. (1995) *Science* 269:496). In contrast, no significant homology was obtained for ORF3 to any other gene product whose sequence is available from the EMBL data base.

The only ORF which was completely localized on this fragment was the central ORF2 with 885 nucleotides, designated as phaG. It starts at position 911 and ends at position 1795. It was preceded by a tentative S/D-sequence separated by eight nucleotides. About 230 bp downstream of the translational stop codon of phaG a potential factor independent transcription terminator is located. Several other ORF's were detected. However, none of them obeyed the rules of Bibb, M. J. et al. (1984) *Gene* 30:157 for a coding region or was preceded by a reliable ribosomal binding site.

EXAMPLE 5

Characterization of the phaG translational product

The codon usages in all three ORF's agreed well with typical *P. putida* codon references, and the G+C content of 59.2 mol% forphaG was similar to the value of 60.7 to 62.5 mol% determined for total genomic DNA of *P. putida* (Rothmel et al. (1991) *Methods Enzymol.* 204:485 and Stanier et al. (1966) *J. Gen. Microbiol.* 43:159) and is closely related to the G+C content of pchC (62.1 mol%), pchF (59.6 mol%) (Kim et al. (1994) *J. Bacteriol.* 176:6349) and other *P. putida* genes (Holloway and Morgan (1986) *Annu. Rev. Microbiol.* 40:79; Misra et al. (1984) *Proc. Natl. Acad. Sci. USA* 81:5979; Nakai et al. (1983) *J. Biol. Chem.* 258:2923).

The phaG gene encodes a protein of 295 amino acids with a molecular weight of 33,876 Da. The deduced amino acid sequence is shown in Sequence Listing SEQ ID NO: 2. Sequence alignments of the amino acid sequence deduced from phaG revealed a 44% overall identity to the rhiA gene product of *Pseudomonas aeruginosa* PG201 (Ochsner et al. (1994) *J. Biol. Chem.* 269:19787). RhlA also consists of 295 amino acids and has a molecular weight of 32.5 kDa. This gene represents the 5'-terminal gene of a gene cluster consisting of the genes rhlA, rhlB, and rhlR. The first two genes represent structural genes encoding proteins involved in rhamnolipid biosynthesis, and RhlR represents a transcriptional activator acting upon $\sigma^{54}$ dependent promoters. The rhlB gene product exhibited rhamnosyltransferase activity whereas the function of RhlA is not yet characterized but is necessary for effective rhamnolipid biosynthesis (Ochsner et al. (1994) *J. Biol. Chem.* 269:19787). The C-terminal region of RhlA and PhaG revealed high homology to a gene region (qin) of *P. aeruginosa* encoding the so-called "quinolone-sensitivity protein" (Tonelli, D. A., and R. V. Miller, unpublished results (GenEMBL data library, accession number L02105). This region comprises 1503 nucleotides. The amino terminus of the qin gene was not exactly determined, and the homology as depicted in the database extends only from nucleotide 207 to 566 of this sequence. However, translation of this sequence in all six reading frames and a subsequent tBLASTn search resulted in the identification of homologies in the upstream region of the suggested qin translational start codons but in different reading frames with the N-terminal region of PhaG and RhlA, respectively. The stop codon occurs 38 amino acids later in the qin gene than in the other genes. The amino acid identity of the qin region amounted to 50.6 and 40.1% to PhaG or to RhlA, respectively, in 249 overlapping residues.

PhaG has an additional, but smaller, region of homology to a group of enzymes, most of which are hydrolases active on esters such as lipids (e.g. triacylglycerol lipase; Rawadi et al. (1995) *Gene* 158:107 or polyhydroxyalkanoates (e.g., PHA depolymerase; Timm and Steinbuchel (1992) *Eur. J. Biochem.* 209:15. This homologous region extends from residues 209–258 of PhaG, and includes a histidine residue (residue 251 of PhaG) that is highly conserved among these proteins. These data suggest a catalytic function for PhaG, perhaps involving breaking of ester bonds. Such an activity could be expected in an acyltransferase, thiokinase, or acyl-CoA ligase.

EXAMPLE 6

Identification and regulation of the promoter 244 bp upstream of phaG a putative $\sigma^{70}$ dependent promoter structure TTGCGC-N17-TTGAAT was identified. The promoter was verified by complementation studies of the PHAG$_{NI}$ mutant 2:1 with subfragments of E3. The 2.2-kbp SalI-EcoRI subfragment (SF22) (FIG. 1), which lacked the above mentioned promoter sequence, did not complement mutant 2:1, whereas the 1.3-kbp BamHI-HindIII subfragment (BH13) (FIG. 2) of E3 conferred the ability to synthesize PHA again from simple carbon sources to this mutant.

Figure 2:
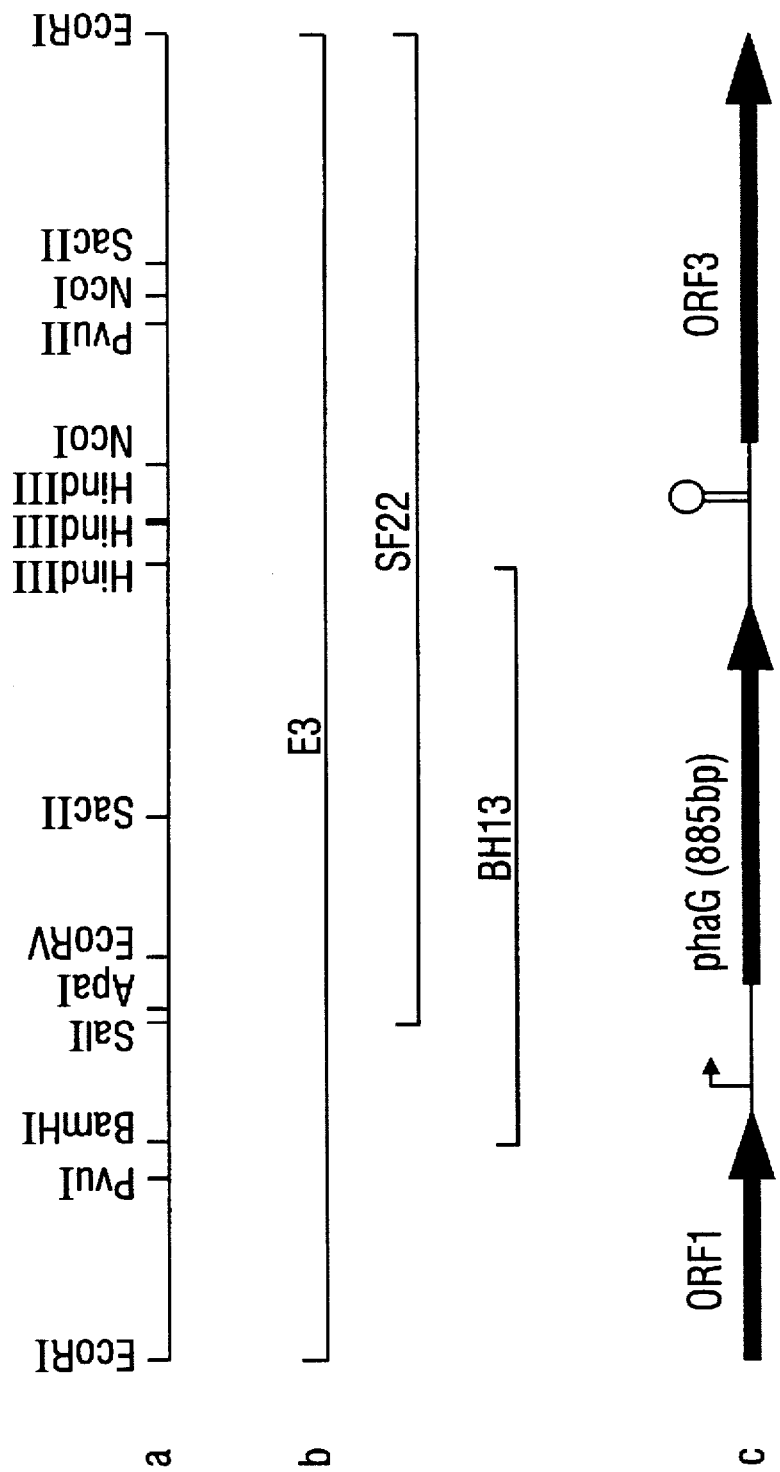
FIG. 2 shows the molecular organization of the P. putida KT2440 phaG gene locus.

In addition, the significance of this putative promoter structure was proved by S 1 nuclease protection with total RNA isolated from gluconate-grown and octanoate-grown cells of *P. putida* KT2440 harvested in the stationary growth phase. The transcriptional start site was identified 5 nucleotides downstream of the putative promoter consensus sequence at position 673 (FIG. 2).

For octanoate-grown cells of *P. putida* KT2440, only an extremely weak RNA signal could be detected, whereas a strong signal was detected with RNA isolated from *A. eutrophus* H16 cells grown on gluconate as carbon source. This result indicated a strong transcriptional induction of phaG under conditions of PHA synthesis via de novo fatty acid biosynthesis.

EXAMPLE 7

Peptides, Polypeptides, and Proteins Biologically Functionally Equivalent To *P. putida* PhaG The present invention includes not only the *P. putida* PhaG protein encoded by the nucleotide sequence shown in SEQ ID NO: 1, positions 911 through 1795, but also biologically functional equivalent peptides, polypeptides, and proteins. The phrase "biologically functional equivalent peptides, polypeptides, and proteins" denotes peptides, polypeptides, and proteins that exhibit the same or similar PhaG activity as the PhaG of *P. putida* when assayed biologically by complementation utilizing a PhaG minus mutant of *Pseudomonas putida* defective in PHA synthesis via growth on simple carbohydrate substrates. By "the same or similar PhaG activity" is meant the ability to perform the same or similar function as PhaG. These peptides, polypeptides, and proteins can contain a region or moiety exhibiting sequence similarity to a corresponding region or moiety of the *P. putida* PhaG protein disclosed herein at SEQ ID NO:2, but this is not required as long as they exhibit the same or similar PhaG activity as that of the *P. putida* PhaG protein.

The PhaG protein is useful not only in the enzymatic synthesis of PHAs, but also as an antigen for the preparation of antibodies that can be used to purify or detect this PhaG protein, or possible other PhaG-like proteins.

Peptides, polypeptides, and proteins biologically functional equivalent to PhaG protein can occur in a variety of forms as described below.

Conservative Amino Acid Changes in the *P. putida* PhaG Amino Acid Sequence

Peptides, polypeptides, and proteins biologically functionally equivalent to PhaG protein include amino acid sequences containing amino acid changes in the fundamental *P. putida* PhaG sequence. The biologically functional equivalent peptides, polypeptides, and proteins of PhaG protein encompassed by the present invention should generally possess at least about 40% sequence similarity, preferably at least about 60% sequence similarity, and most preferably at least about 80% sequence similarity to the naturally occurring protein, or corresponding region or moiety thereof. In this context, "sequence similarity" is determined by the "Gap" or "BestFit" programs of the Sequence Analysis Software Package, Genetics Computer Group, Inc., University of Wisconsin Biotechnology Center, Madison, Wisc. 53711. This software matches similar sequences by assigning degrees of homology to various additions, deletions, substitutions, and other modifications. BestFit makes an optimal alignment of the best segment of similarity between two sequences. Optimal alignments are found by inserting gaps to maximize the number of matches using the local homology algorithm of Smith and Waterman (1981) *Adv. Appl. Math.* 2:482–489. Gap uses the algorithm of Needleman and Wunsch (1970 *J Mol. Biol.* 48:443–453) to find the alignment of two complete sequences that maximizes the number of matches and minimizes the number of gaps.

Fragments and Variants of PhaG

Fragments and variants of *P. putida* PhaG possessing the same or similar PhaG activity as that of *P. putida* PhaG are also encompassed by the present invention.

Fragments of PhaG

Fragments of *P. putida* PhaG can be truncated forms of the enzyme wherein one or more amino acids are deleted from the N-terminal end, C-terminal end, internal region of the protein, or combinations thereof, so long as such fragments retain the same or similar PhaG enzymatic activity as the naturally occurring *P. putida* PhaG. These fragments can be naturally occurring muteins of PhaG, or can be produced by restriction endonuclease treatment or Exonuclease III treatment (Henikoff (1984) *Gene* 28:351) of the encoding nucleotide sequence.

Variants of *P. putida* PhaG

Variants of *P. putida* PhaG include forms of the enzyme wherein one or more amino acids in the naturally occurring amino acid sequence has(have) been substituted with another amino acid, or wherein one or more amino acids has (have) been inserted into the natural amino acid sequence. The variants contemplated herein retain the same or similar PhaG activity as naturally occurring *P. putida* PhaG. These variants can be naturally occurring muteins of PhaG, or can be produced by random mutagenesis of the wild-type encoding nucleotide sequence (Greener et al. (1994) *Strategies* 7:32–34) or by replacing domains thereof with domains of other PhaG of interest. The PhaG activity of such variants can be assayed by complementation as described supra.

Combinations of the foregoing, i.e., forms of PhaG containing amino acid additions, deletions, and substitutions, but which retain the same or similar PhaG activity as naturally occurring *P. putida* PhaG, are also encompassed by the present invention.

Fragments and variants of PhaG encompassed by the present invention should preferably possess at least about 40% sequence similarity, more preferably at least about 60% sequence similarity, and most preferably at least about 80% sequence similarity, to the natural *P. putida* PhaG or corresponding region or moiety thereof. Sequence similarity can be determined using the Gap or BestFit programs of the Sequence Analysis Software Package discussed above.

EXAMPLE 8

Nucleotide Sequences Biologically Functionally Equivalent to Genomic DNA Encoding *P. putida* PhaG The present invention encompasses not only the *P. putida* PhaG genomic DNA sequence shown in SEQ ID NO: 1, but also biologically functional equivalent nucleotide sequences. The phrase "biologically functional equivalent nucleotide sequences" denotes DNAs and RNAs, including genomic DNA, cDNA, synthetic DNA, and mRNA nucleotide sequences, that encode peptides, polypeptides, and proteins exhibiting the same or similar PhaG enzymatic activity as that of *P. putida* PhaG when assayed enzymatically or by complementation. Such biologically functional equivalent nucleotide sequences can encode peptides, polypeptides, and proteins that contain a region or moiety exhibiting sequence similarity to the corresponding region or moiety of the *P. putida* PhaG.

Nucleotide Sequences Encoding Conservative Amino Acid Changes in the *P. putida* PhaG Amino Acid Sequence As noted in Example 7, supra, biologically functional equivalent nucleotide sequences of the present invention include nucleotide sequences that encode conservative amino acid changes within the *P. putida* PhaG amino acid sequence, producing silent changes therein. Such nucleotide sequences thus contain corresponding base substitutions based upon the genetic code compared to wild-type nucleotide sequences encoding *P. putida* PhaG protein.

Nucleotide Sequences Encoding Non-Conservative Amino Acid Substitutions, Additions, or Deletions in *P. putida* PhaG In addition to nucleotide sequences encoding conservative amino acid changes within the naturally occurring *P.*

*putida* PhaG amino acid sequence, biologically functional equivalent nucleotide sequences of the present invention also include genomic DNA, cDNA, synthetic DNA, and mRNA nucleotide sequences encoding non-conservative amino acid substitutions, additions, or deletions. These include nucleic acids that contain the same inherent genetic information as that contained in the genomic PhaG DNA of SEQ ID NO: 1, and which encode peptides, polypeptides, or proteins exhibiting the same or similar PhaG enzymatic activity as that of *P. putida* PhaG. Such nucleotide sequences can encode fragments or variants of *P. putida* PhaG. The *P. putida* PhaG-like enzymatic activity of such fragments and variants can be identified by complementation or enzymatic assays as described above. These biologically functional equivalent nucleotide sequences can possess at least 40% sequence identity, preferably at least 60% sequence identity, and most preferably at least 80% sequence identity, to naturally occurring *P. putida* PhaG genomic DNA, cDNA, synthetic DNA, and mRNA, respectively, or corresponding regions or moieties thereof.

Mutations made in *P. putida* PhaG cDNA, genomic DNA, synthetic DNA, mRNA, or other nucleic acid preferably preserve the reading frame of the coding sequence. Furthermore, these mutations preferably do not create complementary regions that could hybridize to produce secondary mRNA structures, such as loops or hairpins, that would adversely affect mRNA translation.

Although mutation sites can be predetermined, it is not necessary that the nature of the mutations per se be predetermined. For example, in order to select for optimum characteristics of mutants at a given site, site-directed mutagenesis can be conducted at the target codon (Thompson et al. (1988) *Biochemistry* 28:57335), and the PhaG enzymatic activity of the resulting peptide, polypeptide, or protein can be determined enzymatically or by complementation.

In the present invention, nucleic acids biologically functionally equivalent to *P. putida* PhaG genomic DNA having the nucleotide sequence shown in SEQ ID NO: 1 include:

(1) DNAs originating from *P. putida*, exemplified herein by *P. putida* KT2440, the length of which has been altered either by natural or artificial mutations such as partial nucleotide insertion or deletion, or the like, so that when the entire length of the coding sequence within SEQ ID NO:1, positions 911 through 1795, is taken as 100%, the biologically functional equivalent nucleotide sequence has an approximate length of about 60–120% thereof, preferably about 80–110% thereof; or (2) nucleotide sequences containing partial (usually 80% or less, preferably 60% or less, more preferably 40% or less of the entire length) natural or artificial mutations so that such sequences code for different amino acids, but wherein the resulting protein retains the same or similar PhaG enzymatic activity as that of naturally occurring *P. putida* PhaG. The mutated DNAs created in this manner should preferably encode a protein having at least about 40%, preferably at least about 60%, and more preferably at least about 80%, sequence similarity to the amino acid sequence of the *P. putida* PhaG. Sequence similarity can be assessed by the Gap or BestFit programs of the Sequence Analysis Software Package discussed above.

The methods that can be employed to create the artificial nucleic acid mutations contemplated herein are not specifically limited, and can be produced by any of the means conventional in the art. For example, the *P. putida* phaG gene, cDNA, or synthetic DNA can be treated with appropriate restriction enzymes so as to insert or delete desired DNA fragments so that the proper nucleic acid reading frame is preserved. Subsequent to restriction endonuclease treatment, the digested DNA can be treated to fill in any overhangs, and the DNA religated. C-terminal deletions can be produced by Exonuclease III treatment of the DNA. Alternatively, various domains of the *P. putida* PhaG can be replaced with regions of other PhaG proteins by appropriate nucleic acid manipulations employing restriction enzymes, followed by ligation.

Mutations can also be introduced at particular loci by synthesizing oligonucleotides containing a mutant sequence flanked by restriction sites enabling ligation to fragments of the native *P. putida* PhaG genomic DNA, cDNA, or synthetic DNA sequence. Following ligation, the resulting reconstructed sequence encodes a biologically functional equivalent having the desired amino acid insertion, substitution, or deletion.

Alternatively, oligonucleotide-directed site-specific or segment-specific mutagenesis procedures can be employed to produce an altered DNA sequence having particular codons altered according to the insertion, substitution, or deletion required.

Exemplary methods of making the alterations described above are disclosed by Walder et al. (1986) *Gene* 42:133; Bauer et al. (1985) *Gene* 37:73; Craik (January, 1985) *BioTechniques*, pp. 12–19; Smith et al. (1981) *Genetic Engineering: Principles and Methods*, Plenum Press; Ausubel et al. (1989) *Current Protocols in Molecular Biology*, John Wiley & Sons, Inc.; Sambrook et al. (1989) *Molecular Cloning: A Laboratory Manual*, Second Edition, Cold Spring Harbor Laboratory Press, Cold Spring Harbor, N.Y.; Frits Eckstein et al. (1982) *Nucleic Acids Research* 10:6487–6497, and Osuna et al. 1994) *Critical Reviews In Microbiology*, 20:107–116.

Biologically functional equivalents to the genomic DNA sequence disclosed herein produced by any of the foregoing methods can be selected for by complementation or enzymatic assay of the resulting peptides, polypeptides, or proteins as described above.

Alternatively, mutations can be introduced at particular loci by synthesizing oligonucleotides containing a mutant sequence flanked by restriction sites facilitating ligation to fragments of the native *P. putida* PhaG nucleotide sequence. Following ligation, the resulting reconstructed nucleotide sequence encodes a biologically functional equivalent form of synthase having the desired amino acid insertion, substitution, or deletion. The mutant forms so produced can be screened for *P. putida* like PhaG activity by complementation or enzymatic assays.

Useful biologically functional equivalent forms of the genomic phaG DNA of SEQ ID NO:1 include DNAs comprising nucleotide sequences that exhibit a level of sequence identity to corresponding regions or moieties of the genomic phaG DNA of SEQ ID NO:1, positions 911 through 1795, of at least about 40%, preferably at least about 60%, and more preferably at least about 80%. Sequence identity can be determined using the BestFit or Gap programs discussed above.

Genetically Degenerate Nucleotide Sequences

Due to the degeneracy of the genetic code, i.e., the existence of more than one codon for most of the amino acids naturally occurring in proteins, genetically degenerate DNA (and RNA) sequences that contain the same essential genetic information as the genomic DNA of the present invention, and which encode the same amino acid sequence as that of *P. putida* PhaG show in SEQ ID NO:2, are encompassed by the present invention. Genetically degenerate forms of any of the other nucleic acid sequences discussed herein are encompassed by the present invention as well.

Biologically Functional Equivalent Nucleic Acid Sequences Detected by Hybridization Although one embodiment of a nucleotide sequence encoding *P. putida* PhaG is shown in SEQ ID NO:1, positions 711 through 1795, it should be understood that other biologically functional equivalent forms of *P. putida* PhaG-encoding nucleic acids can be readily isolated using conventional DNA—DNA or DNA-RNA hybridization techniques. Thus, the present invention also includes nucleotide sequences that hybridize to SEQ ID NO:1, positions 911 through 1795, and its complementary sequence, and that code on expression for peptides, polypeptides, and proteins exhibiting the same or similar enzymatic activity as that of *P. putida* PhaG. Such nucleotide sequences preferably hybridize to SEQ ID NO:1, positions 911 through 1795, its complementary sequence under moderate to high stringency (see Sambrook et al. (1989) *Molecular Cloning: A Laboratory Manual*, Second Edition, Cold Spring Harbor Laboratory Press, Cold Spring Harbor, N.Y.). Exemplary conditions include initial hybridization in 6X SSC, 5X Denhardt's solution, 100 mg/ml fish sperm DNA, 0.1% SDS, at 55° C. for sufficient time to permit hybridization (e.g., several hours to overnight), followed by washing two times for 15 min. each in 2X SSC, 0.1% SDS, at room temperature, and two times for 15 min. each in 0.5—1X SSC, 0.1% SDS, at 55° C., followed by autoradiography. Typically, the nucleic acid molecule is capable of hybridizing when the hybridization mixture is washed at least one time in 0.1X SSC at 55° C., preferably at 60° C., and more preferably at 65° C.

The present invention also encompasses nucleotide sequences that hybridize to genomic DNA, cDNA, or synthetic DNA molecules that encode the amino acid sequence of *P. putida* PhaG, or genetically degenerate forms thereof due to the degeneracy of the genetic code, under salt and temperature conditions equivalent to those described supra, and that code on expression for a peptide, polypeptide, or protein that has the same or similar PhaG enzymatic activity as that of *P. putida* PhaG.

The nucleotide sequences described above are considered to possess a biological function substantially equivalent to that of the *P. putida* PhaG gene of the present invention if they encode peptides, poly-peptides, or proteins having PhaG activity differing from that of *P. putida* PhaG by about ±30% or less, preferably by about ±20% or less, and more preferably by about ±10% or less when assayed in vivo by complementation.

Biologically Functional Equivalent Nucleic Acid Sequences Detected by Complementation An *E. coli* donor strain harboring a broad host range plasmid comprising a putative biologically functional equivalent nucleic acid in cis with all regulatory elements necessary for expression can be used to conjugate the plasmid into a recipient PhaG-minus bacterial strain by triparental mating using the helper plasmid pRK2013 (Ditta et al. (1980) *Proc. Natl. Acad. Sci. USA* 77:7347). Resulting transconjugants can be selected on polymer-conducive medium supplemented with appropriate antibiotics. Fermentation of the transconjugants in media containing different carbon substrates and subsequent analysis of the resulting PHA provides a means of determining the functional equivalency of the nucleic acid.

Genomic Probes

In another aspect, the present invention provides oligonucleotide hybridization probes useful in screening genomic and other nucleic acid libraries for DNA sequences encoding peptides, polypeptides, or proteins having enzymatic activity the same or similar to that of *P. putida* PhaG, which probes can be designed based on the sequences provided in SEQ ID NO:1, positions 911 through 1795. Such probes can range from about 20 to about 60 nucleotides in length, generally about 20 nucleotides in length, more typically about 30 nucleotides in length, preferably about 40 nucleotides in length, and more preferably about 50–60 nucleotides in length. Preferably, these probes specifically hybridize to *P. putida* genomic phaG DNA and other DNA sequences encoding peptides, polypeptides, or proteins having the same or similar PhaG activity as that of *P. putida* PhaG under hybridization conditions such as those described above. Such oligonucleotide probes can be synthesized by automated synthesis, and can be conveniently labeled at the 5' end with a reporter such as a radionuclide, e.g., $^{32}P$, or biotin. The library to be probed can be plated as colonies or phage, depending upon the vector employed, and the recombinant DNA transferred to nylon or nitrocellulose membranes. Following denaturation, neutralization, and fixation of the DNA to the membrane, the membrane is hybridized with the labeled probe. Following this, the membrane is washed, and the reporter molecule detected. Colonies or phage harboring hybridizing DNA are then isolated and propagated. Candidate clones or PCR-amplified fragments can be verified as comprising DNA encoding *P. putida*-like PhaG activity or related peptides, polypeptides, or proteins having activity the same as or similar to *P. putida* PhaG by a variety of methods. For example, the candidate clones can be hybridized with a second, non-overlapping probe, or subjected to DNA sequence analysis. The activity of the peptide, polypeptide, or protein encoded thereby can be assessed by cloning and expression of the DNA in an appropriate host such as *E. coli*, followed by isolation of the peptide, polypeptide, or protein and assay of the activity thereof. By such means, nucleic acids encoding PhaG proteins from microorganisms other than *P. putida*, as well as peptides, polypeptides, and proteins biologically functionally equivalent to *P. putida* PhaG, useful in producing PHAs, can be isolated.

Degenerate Oligonucleotide Primers

Biologically functional equivalent phaG genes from other microorganisms, or equivalent PhaG-encoding cDNAs or synthetic DNAs, can also be isolated by amplification using Polymerase Chain Reaction (PCR) methods. Degenerate oligonucleotide primers based on the amino acid sequence of *P. putida* PhaG can be prepared and used in conjunction with PCR technology employing reverse transcriptase (E. S. Kawasaki (1990), In Innis et al., Eds., *PCR Protocols*, Academic Press, San Diego, Chapter 3, p. 21) to amplify biologically functional equivalent DNAs from genomic or cDNA libraries of other organisms.

Alternatively, the degenerate oligonucleotides can be used as probes to screen CDNA libraries in, for example, λ phage vectors such as λ Zap.II (Stratagene).

EXAMPLE 9

Heterologous overexpression of phaG in *E. coli*

To ensure heterologous expression of PhaG in *E. coli*, the T7-polymerase expression vector pT7-7 (Tabor and Richardson (1991) *Proc. Natl. Acad. Sci. USA* 82:1074) was used. To connect the phaG gene to the transcription/translation initiation region of pT7-7 a NdeI-site was created at the start codon of phaG by PCR amplification. The 0.97-kbp PCR product was digested with NdeI and HindIII and ligated to the likewise digested vector. The sequence of this construct, which was designated pT7-G1, was confirmed, and it was transformed to *E. coli* BL21 (DE3) (Studier and Moffatt (1986) *J. Mol. Biol.* 189:113), which carried the gene for the T7 polymerase under the control of an IPTG (isopropyl-β-D-thiogalactopyranoside)-inducible lacUV5 promoter. Cells harboring pT7-G1 and cells harboring pT7-7 (negative control) were cultivated in LB-medium containing 100 μl of ampicillin per ml. The expression of the T7 RNA polymerase was induced at an optical density of 1.0 at 500 nm by adding IPTG to a final concentration of 0.4 mM. After four hours of incubation cells were harvested and lysed by sonification. Cells harboring pT7-G1 produced during induction high amounts of inclusion bodies, which were partially separated from crude extracts by fractionated centrifugation at 5,000 x g, and 3,000 x g, respectively, and subsequent washing in water. Electropherograms of SDS-polyacrylamide gel electrophoresis revealed one major band with an estimated molecular mass of 34 kDa in the crude extract, the pellet fraction, and the inclusion body preparation obtained from cultures of *E. coli* BL21 (DE3) containing plasmid pT7-G1. This band was absent in the soluble fraction of pT7-G1 harboring *E. coli* cells, as well as in the control preparations of *E. coli* BL21 harboring pT7-7 without insert. The results indicated that PhaG was strongly overexpressed but only in insoluble protein aggregates.

PhaG overexpressed by the T7 expression system can be utilized for numerous applications. For example, the protein produced can be used for antibody production, X-ray crystallography studies, in vitro analysis of PhaG activity, as well as in vitro synthesis of PHA's when combined with the appropriate enzymatic activities. Other expression systems can also be utilized to overexpress PhaG in recombinant systems. For example, the tac promoter of *E. coli* is a useful promoter for expression of PhaG in *E. coli* and other bacteria. Other promoters useful for the expression of PhaG in recombinant hosts are known to those skilled in the art. Protein expressed from the tac promoter may be suitable for in vivo production of PHA from simple carbon sources, for example, glucose, when combined with the appropriate PHA biosynthetic enzymes in a suitable host organism. Antibodies recognizing PhaG can be employed to screen organisms containing PhaG or PhaG like proteins. The antibodies would also be valuable for immuno-purification of PhaG and PhaG like proteins from crude extracts.

EXAMPLE 10

Production of Polyhydroxyalkanoates in Bacteria and Plants Expressing the *P. putida* PhaG Protein The PhaG-encoding DNA of *P. putida* can be introduced into and expressed in a variety of different eukaryotic and prokaryotic cells, for example bacterial and plant host cells, to facilitate the production of PHAs therein. It should be understood that reference to the *P. putida* PhaG and genomic DNA encoding the same in this context includes the biologically functional equivalents thereof, respectively, discussed above. The advantages of this approach to the production of PHAs include decreasing the dependence on petroleum-derived monomers, and the ease with which bacteria and plants can be grown on a large scale.

Optimal PHA synthesis via de novo fatty acid biosynthesis in bacteria and plants comprises at least two genes: PHA synthase (phaC) and phaG (disclosed herein). Methods for incorporating PHA synthase and other PHA genes (phaA (β-ketothiolase) and phaB (D-reductase)) genes into transformation and expression vector constructs and introducing these constructs into bacterial and plant host cells to produce PHAs in such cells are well known in the art. Poirier et al. ((1995) *Bio/Technology* 13:142–150) have recently provided an extensive review of progress in this area. In general, such vector constructs comprise assemblies of DNA fragments operatively linked in a functional manner such that they drive the expression of the structural DNA sequences contained therein. These vector constructs usually contain a promoter that functions in the selected host cell, along with any other necessary regulatory regions such as ribosome binding sites, transcription terminators, 3' non-translated polyadenylation signals, etc., linked together in an operable manner, as well as selectable markers (Sambrook et al., *Molecular Cloning: A Laboratory Manual*, Second Edition, 1989, Cold Spring Harbor Laboratory Press, Cold Spring Harbor, N.Y.; Ausubel et al. (1989) *Current Protocols in Molecular Biology*, John Wiley & Sons, Inc.).

Such vectors can be introduced into bacterial cells, for example, by calcium chloride/heat shock treatment or electroporation. Transformed host cells can subsequently be selected for on selective media, cultured in an appropriate medium under conditions conducive to the production of PHA, and the PHA can then be recovered from the cells. Representative methods have been described by Slater et al. (1988) *J. Bacteriol.* 170:4431–4436; Slater et al. (1992) *Appl. Environ. Microbiol.* 58:1089–1094; Zhang et al. (1994) *Appl. Environ. Microbiol.* 60:1198–1205; and Kidwell et al. (1995) *Appl. Environ. Microbiol.* 61:1391–1398.

Useful hosts for PHA polymer production employing PhaG include Actinomycetes (e.g., Streptomyces sp. and Nocardia sp.); other bacteria (e.g., Alcaligenes (e.g., *A. eutrophus*), *Bacillus cereus*, *B. subtilis*, *B. licheniformis*, *B. megaterium*, *Escherichia coli*, Klebsiella sp. (e.g., *K. aerogenes* and *K. oxytoca*), Lactobacillus, Methylomonas, Pseudomonas sp. (e.g., *P. putida* and *P. fluorescens*) Nocardia sp. (e.g., *N. corallina*), and Rhodospirillum sp. (e.g., *R. rubrum*).; fungi (e.g., Aspergillus, Cephalosporium, and Penicillium); and yeast (e.g., Saccharomyces, Rhodotorula, Candida, Hansenula, and Pichia).

Other useful bacteria strains include those strains capable of high accumulation of lipids and strains that have high conversion rates of simple carbon sources to acetyl-CoA.

In plants, transformation vectors capable of introducing bacterial genes involved in PHA biosynthesis can be designed. Generally, such vectors comprise one or more coding sequences of interest under the transcriptional control of 5' and 3' regulatory sequences, including a promoter, and a selectable marker. Typical regulatory sequences include a transcription initiation start site, an RNA processing signal, a transcription termination site, and/or a polyadenylation signal. Plant promoter can be inducible or constitutive, environmentally- or developmentally-regulated, or cell- or tissue-specific. Often-used promoters include the CaMV 35S promoter (Odell et al. (1985) *Nature* 313:810), the enhanced CaMV 35S promoter, the Figwort Mosaic Virus (FMV) promoter (Richins et al. (1987) NAR 20:8451), the mannopine synthase (mas) promoter, the nopaline synthase (nos) promoter, and the octopine synthase (ocs) promoter. Useful inducible promoters include heat-shock promoters (Ou-Lee et al. (1986) *Proc. Natl. Acad. Sci. USA* 83:6815; a nitrate-inducible promoter derived from the spinach nitrite reductase gene (Back et al. (1991) *Plant Mol. Biol.* 17:9); hormone-inducible promoters (Yamaguchi- Shinozaki et al. (1990) *Plant Mol. Biol.* 15:905; Kares et al. (1990) *Plant Mol. Biol.* 15:905), and light-inducible promoters associated with the small subunit of RuBP carboxylase and LHCP gene families (Kuhlemeier et al. (1989) *Plant Cell* 1:471; Feinbaum et al. (1991) *Mol. Gen. Genet.* 226:449; Weisshaar et al. (1991) *EMBO J.* 10:1777; Lam and Chua (1990) *Science* 248:471; Castresana et al. (1988) *EMBO J.* 7:1929; Schulze-Lefert et al. (1989) *EMBO J.* 8:651). Examples of useful tissue-specific, developmentally-regulated promoters include the β-conglycinin 7S promoter (Doyle et al. (1986) *J. Biol. Chem.* 261:9228; Slighton and Beachy (1987) *Planta* 172:356), and seed-specific promoters (Knutzon et al. (1992) *Proc. Natl. Acad. Sci. USA* 89:2624; Bustos et al. (1991) *EMBO J.* 10:1469; Lam and Chua (1991) *Science* 248:471; Stayton et al. (1991) *Aust. J. Plant. Physiol.* 18:507). Plant functional promoters useful for preferential expression in seed plastids include those from plant storage protein genes and from genes involved in fatty acid biosynthesis in oilseeds. Examples of such promoters include the 5' regulatory regions from such genes as napin (Kridl et al. (1991) *Seed Sci. Res.* 1:209), phaseolin, zein, soybean trypsin inhibitor, ACP, stearoyl-ACP desaturase, and oleosin. Seed-specific gene regulation is discussed in EP 0 255 378. Promoter hybrids can also be constructed to enhance transcriptional activity (Hoffman, U.S. Pat. No. 5,106,739), or to combine desired transcriptional activity and tissue specificity. Representative vectors often comprise, operatively linked in sequence in the 5' to 3' direction, a promoter sequence that directs the transcription of a downstream heterologous structural DNA in a plant; optionally, a non-translated leader sequence; a nucleotide sequence that encodes a protein of interest; and a 3' non-translated region that encodes a polyadenylation signal which functions in plant cells to cause the termination of transcription and the addition of polyadenylate nucleotides to the 3' end of the mRNA encoding said protein. Additionally, a factor to consider is the timing and intracellular localization of PhaG expression and other enzymes necessary for the biosynthesis of PHA. For example, if fatty acid biosynthetic pathways are utilized in oilseed plants such as canola, then PhaG expression should be concurrent with fatty acid biosynthesis and targeted to the seed leucoplast or leaf chloroplast.

A variety of different methods can be employed to introduce such vectors into plant protoplasts, cells, callus tissue, leaf discs, meristems, etc., to generate transgenic plants, including Agrobacterium-mediated transformation, particle gun delivery, microinjection, electroporation, polyethylene glycol-mediated protoplast transformation, liposome-mediated transformation, etc. (reviewed in Potrykus (1991) *Annu. Rev. Plant Physiol. Plant Mol. Biol* 42:205–225). In general, transgenic plants comprising cells containing and expressing *P. putida* PhaG-encoding DNA can be produced by transforming plant cells with a DNA construct as described above via any of the foregoing methods; selecting plant cells that have been transformed on a selective medium; regenerating plant cells that have been transformed to produce differentiated plants; and selecting a transformed plant which expresses the *P. putida* PhaG-encoding nucleotide sequence.

The encoding DNAs can be introduced either in a single transformation event (all necessary DNAs present on the same vector), a co-transformation event (all necessary DNAs present on separate vectors that are introduced into plants or plant cells simultaneously), by independent transformation events (all necessary DNAs present on separate vectors that are introduced into plants or plant cells independently) or by re-transformation (transforming an already transformed line generated by a single transformation, co-transformation, or independent transformation events). Traditional breeding methods, when applicable, can subsequently be used to incorporate the entire pathway into a single plant. Successful production of the PHA polyhydroxybutyrate in cells of Arabidopsis has been demonstrated by Poirier et al. (1992) *Science* 256:520–523, and in plastids thereof by Nawrath et al. (1994) *Proc. Natl. Acad. Sci. USA* 91:12760–12764.

Specific methods for transforming a wide variety of dicots and obtaining transgenic plants are well documented in the literature (see Gasser and Fraley (1989) *Science* 244:1293; Fisk and Dandekar (1993) *Scientia Horticulturae* 55:5–36; Christou (1994) *Agro Food Industry Hi Tech* (March/April 1994) p.17, and the references cited therein).

Successful transformation and plant regeneration have been achieved in the monocots as follows: asparagus (*Asparagus officinalis*; Bytebier et al. (1987) *Proc. Natl. Acad. Sci. USA* 84:5345 ); barley (*Hordeum vulgarae*; Wan and Lemaux (1994) *Plant Physiol.* 104:37); maize (*Zea mays*; Rhodes et al. (1988) *Science* 240:204; Gordon-Kamm et al. (1990) *Plant Cell* 2:603; Fromm et al. (1990) *Bio/Technology* 8:833; Koziel et al. (1993) *Bio/Technology* 11:194); oats (*Avena sativa*; Somers et al. (1992) *Bio/Technology* 10:1589); orchardgrass (*Dactylis glomerata*; Horn et al. (1988) *Plant Cell Rep.* 7:469); rice (*Oryza sativa*, including indica and japonica varieties; Toriyama et al. (1988) *Bio/Technology* 6:10; Zhang et al. (1988) *Plant Cell Rep.* 7:379; Luo and Wu (1988) *Plant Mol. Biol. Rep.* 6:165; Zhang and Wu (1988) *Theor. Appl. Genet.* 76:835; Christou et al. (1991) *Bio/Technology* 9:957); rye (*Secale cereale*; De la Pena et al. (1987) *Nature* 325:274); sorghum (*Sorghum bicolor*; Cassas et al. (1993) *Proc. Natl. Acad. Sci. USA* 90:11212); sugar cane (Saccharum spp.; Bower and Birch (1992) *Plant J.* 2:409); tall fescue (*Festuca arundinacea*; Wang et al. (1992) *Bio/Technology* 10:691); turfgrass (*Agroslis palustris*; Zhong et al. (1993) *Plant Cell Rep.* 13:1); and wheat (*Triticum aestivum*; Vasil et al. (1992) *Bio/Technology* 10:667; Troy Weeks et al. (1993) *Plant Physiol.* 102:1077; Becker et al. (1994) Plant J. 5:299).

Particularly useful plants for PHA polymer production include those, such as potato and sugarbeet, that produce carbon substrates which can be employed for PHA biosynthesis. Cereal plants such as corn, wheat, and rice are also preferred. Other useful plants include tobacco and high oil seed plants such as soybean, canola, oil seed rape, Arabidopsis sp. and peanut. Plants that grow in desert or in mineralized soil can also be employed for the production of PHA. Polymers that can be produced in this manner include but are not limited to for example, PHB, and copolymers incorporating both short chain length and medium chain length monomers, such as PHB-co-PHC, PHC-co-PHO, PHO-co-PHD.

The invention being thus described, it will be obvious that the same can be varied in many ways. Such variations are not to be regarded as a departure from the spirit and scope of the present invention, and all such modifications as would be obvious to one skilled in the art are intended to be included within the scope of the following claims.

What is claimed is:

1. An isolated DNA molecule comprising a nucleotide sequence selected from the group consisting of:
   (a) the nucleotide sequence of the coding strand shown in SEQ ID NO: 1, positions 911 through 1795, or the complement thereof;
   (b) a nucleotide sequence that hybridizes to said nucleotide sequence of (a) under a wash stringency equivalent to 0.5X SSC to 2X SSC, 0.1% SDS, at 55°–65° C., and which encodes a PHA synthase protein;
   (c) a *Pseudomonas putida* nucleotide sequence having at least 40% identity with the nucleotide sequence of (a) and which encodes a PHA synthase protein;
   (d) a nucleotide sequence encoding the same amino acid sequence as said nucleotide sequence of (a); and
   (e) a nucleotide sequence encoding the same amino acid sequence as said nucleotide sequence of (b).

2. The DNA molecule of claim 1 having the DNA sequence of SEQ ID NO: 1, positions 911 through 1795.

3. A recombinant DNA comprising a DNA molecule of claim 1 and a promoter region, operatively linked such that the promoter enhances transcription of said DNA molecule in a host cell.

4. The recombinant DNA of claim 3 wherein said DNA molecule has the DNA sequence of SEQ ID NO: 1, positions 911 through 1795.

5. A recombinant vector comprising a DNA of any one of claims 1–4.

6. A recombinant host cell comprising a DNA of claims 3 or 4, wherein said DNA molecule is heterologous to said promoter region.

7. The recombinant cell of claim 6 which is a microbe or plant cell.

8. The recombinant cell of claim 6 which is a *Pseudomonas fluorescens* rRNA homology group I bacterium.

9. A method of transforming a host cell capable of producing polyhydroxyalkanoates comprising:
   providing a host cell having a functional PHA synthase gene;
   preparing a recombinant vector comprising a DNA molecule of claim 1 and a promoter region, operatively linked such that the promoter causes transcription of said DNA molecule in said host cell, and wherein said DNA molecule is heterologous to said promoter region;
   and transforming the host cell with said vector.

10. The method of claim 9 wherein the recombinant vector comprises a DNA molecule having the nucleotide sequence of SEQ ID NO:1, positions 911 through 1795.

11. The method of claim 9 wherein the host cell is a microbe or a plant cell.

12. The method of claim 9 wherein the host cell is selected from bacteria of the *Pseudomonas fluorescens* rRNA homology group I.

13. A method for preparing polyhydroxyalkanoates composed of repeating units having 3–14 carbon atoms (PHA) comprising:
   culturing transformed cells produced according to any one of claims 9–12 to allow expression of the pha genes; and recovering the PHA from the cells.

14. The method of claim 13 wherein the transformed cells are cultured in a media containing a simple carbohydrate substrate.

15. The method of claim 14 wherein the media comprises gluconate, glucose, sucrose, fructose or lactose.

16. The method of claim 13 wherein the transformed cells are cultured in a media comprising corn syrup or molasses.

17. A substantially purified protein having the amino acid sequence of SEQ ID NO:2.

18. A method of producing a genetically transformed plant which expresses PhaG comprising the steps of:
   inserting into the genome of a host plant cell a recombinant, double-stranded DNA molecule comprising:
   (i) a promoter which functions in plant cells to enhance transcription of an adjacent DNA coding sequence;
   (ii) a DNA molecule of claim 1 operatively linked to the promoter; and regenerating a genetically transformed plant from said host plant cell.

19. The method of claim 18 wherein the DNA molecule is SEQ ID NO:1, positions 911 through 1795.

20. The method of claim 18 wherein the genome of the host plant cell also includes a functional PHA synthase gene.

21. The method of claim 18 further comprising harvesting the transformed plant or plant parts.

22. The method of claim 21 wherein the plant parts comprise leaves, roots, seeds or tubers.

23. The method of claim 18 wherein the plant is maize, potato, sugar beet, tobacco, wheat, or Arabidonsis; or a high oil seed plant selected from the group consisting of soybean, canola, rape seed, sunflower, flax and peanut.

24. A plant produced by the method of any one of claims 18–20 or 23.

25. A mutant *Pseudomonas putida* microorganism unable to synthesize PHA from gluconate but able to synthesize PHA from octanoic acid.

26. The mutant of claim 25 wherein the phenotypic ability to synthesize PHA from gluconate is restored by complementation with a DNA sequence of SEQ ID NO: 1.

* * * * *

UNITED STATES PATENT AND TRADEMARK OFFICE
CERTIFICATE OF CORRECTION

PATENT NO. : 5,750,848
DATED : MAY 12, 1998
INVENTOR(S) : Niels Krüger/Alexander Steinbüchel It is certified that error appears in the above-identified patent and that said Letters Patent is hereby corrected as shown below:

In column 3, lines 58-59, please delete "deduced amino acid sequence of the PhaG protein from *P. putida* KT2440." and insert therefor --nucleotide sequence of fragment E3; the coding strands of the *phaG* encoding DNA fragment is shown at positions 911 through 1795.--

In column 3, lines 60-63, please delete "nucleotide sequence of fragment E3; the coding strands of the phaG encoding DNA fragment is shown at positions 911 through 1795." and insert therefor -- deduced amino acid sequence of the *PhaG* protein from *P. putida* KT2440.--

In claim 13, line 47, "pha" should read --*pha*--

In claim 23, line 12, "Arabidonsis" should read --*Arabidopsis*--.

Signed and Sealed this

Fifth Day of January, 1999

Attest:

*Attesting Officer*

*Acting Commissioner of Patents and Trademarks*